(12) United States Patent
Kuwabara et al.

(10) Patent No.: US 7,217,827 B2
(45) Date of Patent: May 15, 2007

(54) HALOGEN-CONTAINING AROMATIC COMPOUND

(75) Inventors: Masayoshi Kuwabara, Ibaraki (JP); Yasunori Okumura, Toride (JP)

(73) Assignee: Nippon Shokubai Co., Ltd., Osaka (JP)

( * ) Notice: Subject to any disclaimer, the term of this patent is extended or adjusted under 35 U.S.C. 154(b) by 124 days.

(21) Appl. No.: 10/995,581

(22) Filed: Nov. 23, 2004

(65) Prior Publication Data

US 2005/0090691 A1 Apr. 28, 2005

Related U.S. Application Data

(63) Continuation of application No. 10/133,158, filed on Apr. 26, 2002, now Pat. No. 6,916,959.

(30) Foreign Application Priority Data

| May 11, 2001 | (JP) | ............................. 2001-142028 |
| May 11, 2001 | (JP) | ............................. 2001-142029 |
| May 11, 2001 | (JP) | ............................. 2001-142031 |
| May 11, 2001 | (JP) | ............................. 2001-142032 |

(51) Int. Cl.
*C07D 493/00* (2006.01)
(52) U.S. Cl. ................................. 549/241
(58) Field of Classification Search ............. 549/241
See application file for complete search history.

(56) References Cited

U.S. PATENT DOCUMENTS

| 3,549,591 A | 12/1970 | Griffith ...................... 549/512 |
| 3,975,424 A | 8/1976 | Fujii et al. .............. 260/465 G |
| 4,684,734 A | 8/1987 | Kaieda et al. ............. 546/345 |
| 5,130,490 A | 7/1992 | Albright .................... 564/438 |
| 5,233,018 A | 8/1993 | Ando et al. ................ 528/353 |
| 5,449,741 A | 9/1995 | Ando et al. ................ 528/353 |
| 5,750,731 A | 5/1998 | Ando et al. ................ 549/241 |
| 5,849,934 A | 12/1998 | Ando et al. ................ 549/241 |
| 6,048,986 A | 4/2000 | Ando et al. ................ 549/239 |

FOREIGN PATENT DOCUMENTS

| EP | 0 120 575 A1 | 10/1984 |
| GB | 1168494 | 3/1968 |
| JP | 06-016615 | 1/1994 |
| JP | 06-016656 | 1/1994 |
| JP | 08-333322 | 12/1996 |
| JP | 09-110784 | 4/1997 |
| JP | 09-110785 | 4/1997 |
| JP | 2691995 | 9/1997 |
| JP | 2001-226329 | 8/2001 |

OTHER PUBLICATIONS

Selivanova et al., "Catalytic and Noncatalytic Ammonolysis of Chloropentafluorobenzene", Russian Journal of Organic Chemistry 37:404-409, 2001.

*Primary Examiner*—Kamal A. Saeed
(74) *Attorney, Agent, or Firm*—Fish & Richardson P.C.

(57) ABSTRACT

The present invention relates to halogen-containing aromatic compounds and methods thereof. The present invention relates a halogen-containing aromatic acid dianhydride, halogen-containing aromatic tetranitrile compound, halogen-containing m-phenylenediamine compound and fluorine compound, and a method thereof.

4 Claims, 9 Drawing Sheets

HALOGEN-CONTAINING AROMATIC COMPOUND

Under 35 USC § 120, this application is a continuation application of U.S. application Ser. No. 10/133,158 filed on Apr. 26, 2002, now U.S. Pat. No. 6,916,959, which in turn claims foreign priority under 35 U.S.C. 119 to applications filed in Japan, serial number 2002-142028, filed May 11, 2001, Japan serial number 2001-142029, filed May 11, 2001, Japan serial number 2001-142031, filed May 11, 2001, and Japan serial number 2001-142032, filed May 11, 2001.

BACKGROUND OF THE INVENTION

1. Field of the Invention

The present invention relates to halogen-containing aromatic compounds and methods therefor. More specifically, the present invention relates to a halogen-containing aromatic acid dianhydride (HAA), a halogen-containing aromatic tetranitrile compound (HTC), a halogen-containing aromatic tetracarboxylic acid, a halogenated m-phenylenediamine compound (HPC), and a fluorine compound, and methods therfor.

2. Description of Related Art (HAA; HTC)

Heretofore, halogen-, in particular fluorine-containing aromatic compounds are known to be useful as raw materials for resins which are superior in heat resistance, chemical resistance, water repellent property and low dielectric property. These resin materials are lightweights compared to conventional inorganic materials. These materials have characters that these excel in shock resistance and workability, and are readily handled. For these reasons, these materials have been used for wiring base plate, photosensitive and liquid crystal materials.

The conventional halogen-containing aromatic compounds are produced by replacing a straight chain hydrocarbon group, such as perfluoroalkyl and perfluoroalkenyl groups, with an aromatic ring. However, there is a drawback that heat resistance become lowered by the introduction of such a group.

For introducing a halogen therein without lowering heat resistance, it is considered that halogens are directly replaced with groups of aromatic rings. Direct replacement of halogens with groups of aromatic rings is not well known.

(HPC; Fluorine Compound)

Tetrafluoro m-phenylenediamine and halogenated m-phenylenediamine compounds are important intermediates for synthesizing dye, medicine, agricultural chemical and macromolecule compounds, and useful for raw materials of resins excellent in heat resistance, water repellent property, chemical resistance, and low dielectric property. Furthermore, these are suitably used for charge-transfer agents (in particular positive hole-transfer agents) in the fields of solar battery, electroluminescent elements, and electrophotography photosensitive body.

For this purpose, m-phenylenediamine derivatives and methods thereof are being popularly researched and developed now.

SUMMARY OF THE INVENTION (HAA)

The present invention has been made in view of the above situation. An object of the present invention is to provide a halogen-containing aromatic acid dianhydride useful for raw materials of resins excellent in heat resistance, chemical resistance, water repellent property and low dielectric property.

The present object has been achieved by a halogen-containing aromatic acid dianhydride represented by the formula 1:

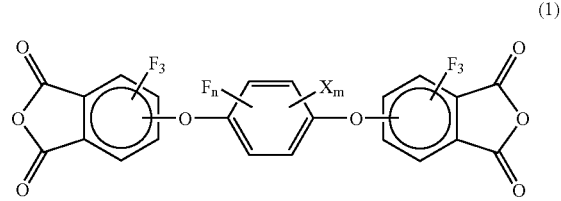

(1)

wherein X is a chlorine, bromine or iodine atom, m an integer of 1 to 4, n an integer of 0 to 3, and the sum of n and m 4.

(HTC)

The present invention has been achieved in view of the above situation. An object of the present invention is to provide a halogen-containing aromatic tetracarboxylic acid and a halogen-containing aromatic tetranitrile compound, which are useful for raw materials of halogen-containing aromatic acid dianhydrides, and a method for the production thereof.

As a result of diligent investigations regarding raw materials used in the production for such halogen-containing aromatic acid dianhydrides, we have found that such dianhydrides can be produced in a high yield by hydrolyzing a halogen-containing aromatic tetranitrile compound having a specified structure and then dehydrating the resulting halogen-containing aromatic tetracarboxylic acid. In addition, as a result of diligent investigations regarding raw materials used in the production for such a halogen-containing aromatic tetranitrile compound, we have found that the halogen-containing aromatic tetranitrile compound can be suitably used, which compound is obtained by the reaction of tetrafluorophthalonitrile and a hydroquinone derivative having a specified structure.

The objects of the present invention have been achieved by the following 1 to 5.

(1) A halogen-containing aromatic tetranitrile compound represented by the formula 21:

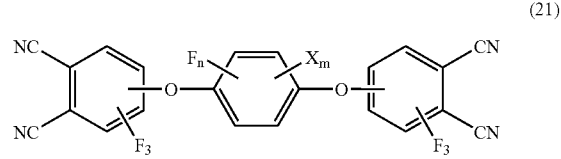

(21)

wherein X is a chlorine, bromine or iodine atom, m an integer of 1 to 4, n an integer of 0 to 3, and the sum of n and m 4.

(2) A halogen-containing aromatic tetracarboxylic acid represented by the formula 22:

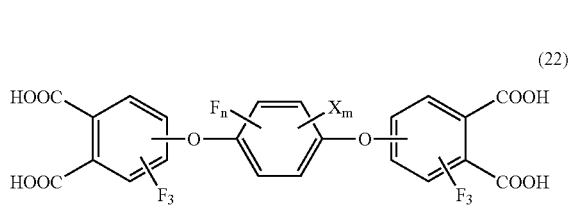

(22)

wherein X is a chlorine, bromine or iodine atom, m an integer of 1 to 4, n an integer of 0 to 3, and the sum of n and m 4.

(3) A method for producing a halogen-containing tetranitrile compound represented by the formula 21, characterized by reacting tetrafluorophthalonitrile with a hydroquinone derivative represented by the formula 23:

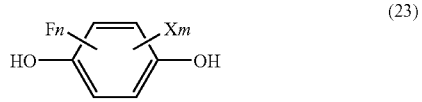

(23)

wherein X is a chlorine, bromine or iodine atom, m an integer of 1 to 4, n an integer of 0 to 3, and the sum of n and m 4.

(4) A method for producing a halogen-containing tetracarboxylic acid represented by the formula 22, characterized by hydrolyzing a halogen-containing aromatic tetranitrile compound represented by the formula 21.

(5) A method for producing a halogen-containing aromatic tetracarboxylic acid dianhydride represented by the formula 1:

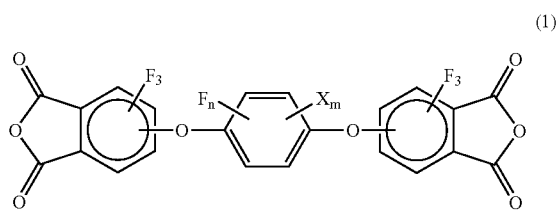

(1)

wherein X is a chlorine, bromine or iodine atom, m an integer of 1 to 4, n an integer of 0 to 3, and the sum of n and m 4, characterized by dehydrating a halogen-containing aromatic tetracarboxylic acid represented by the formula 22.

(HPC)

An object of the present invention is to provide a new halogenated m-phenylenediamine compound.

The object of the present invention has been achieved by a halogenated m-phenylenediamine compound represented by the formula 31:

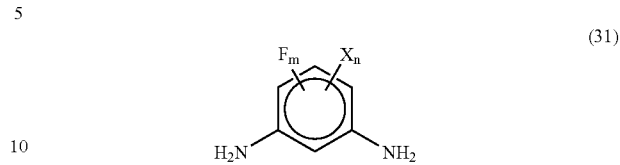

(31)

wherein X is a chlorine or bromine atom, m an integer of 1 to 3, n an integer of 3 to 1, and the sum of n and m 4.

(Fluorine Compound)

An object of the present invention is to provide a new fluorine compound used for producing m-phenylenediamine derivatives.

The object of the present invention has been achieved by a fluorine compound represented by the formula 41:

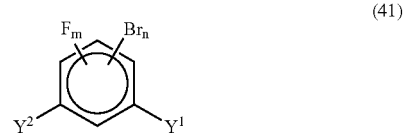

(41)

wherein $Y^1$ and $Y^2$ are independently a carboxyl or cyano group, m is an integer of 1 to 3, n an integer of 3 to 1, and the sum of n and m 4.

The above and other objects, features and advantages of the present invention will become clear from the following description of the preferred embodiments.

BRIEF DESCRIPTION OF DRAWINGS

The accompanying drawing incorporated in and forming a part of the specification, illustrates several aspects of the present invention, and together with the description serve to explain the principles of the invention. In the drawings.

DETAILED DESCRIPTION OF THE PREFERRED EMBODIMENTS (HAA)

Figure 1:
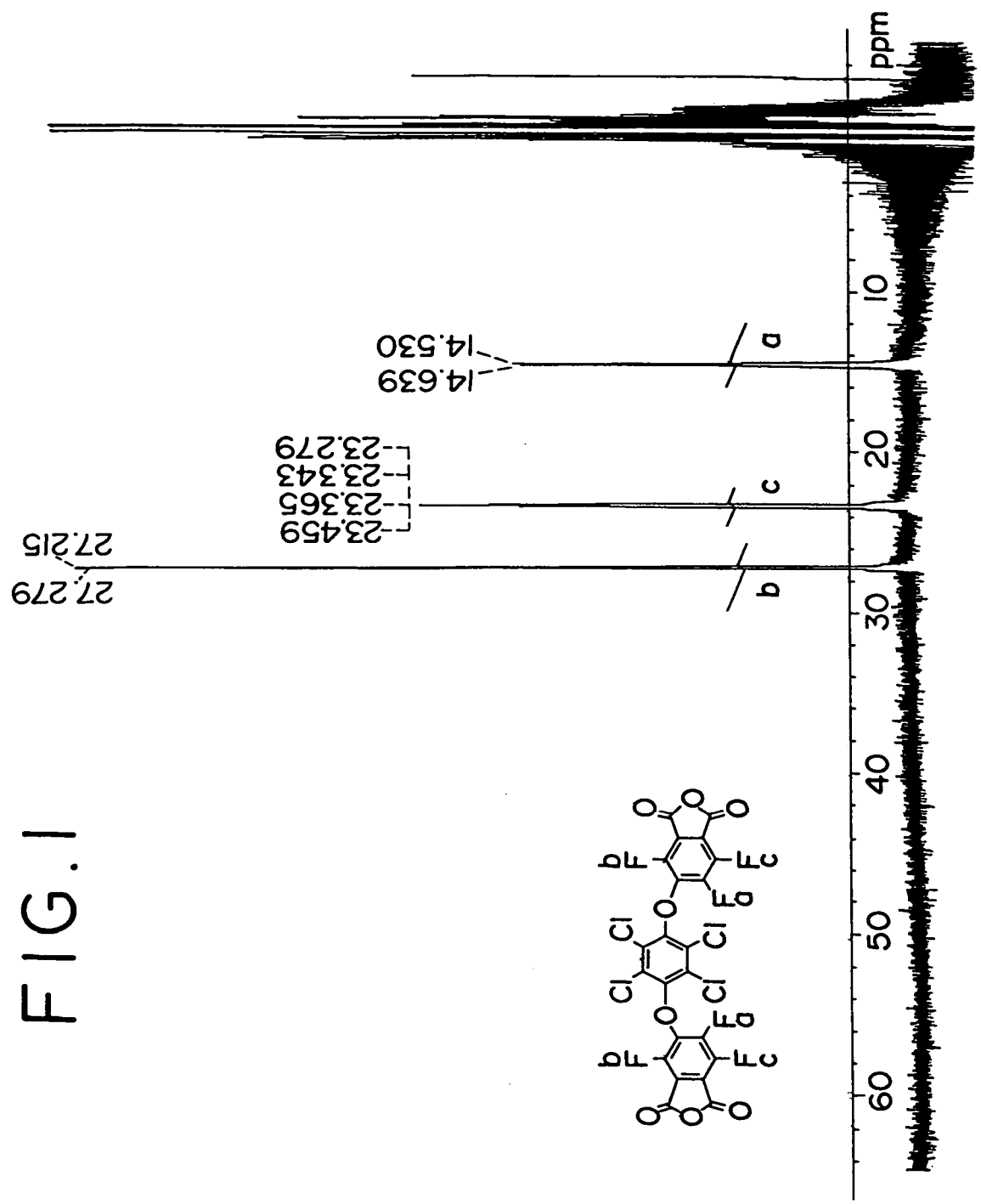
FIG. 1 shows a graph of $^{19}$F-NMR spectrum for 1,4-bis (3,4-dicarboxytrifluorophenoxy)tetrachlorobehzene dianhydride obtained in Example 1 of the present invention.

In view of diligent investigations regarding several kinds of materials, we have known that the halogen-containing aromatic acid dianhydride having a specified structure excels in heat resistance, chemical resistance, water repellent property and low dielectric property, and therefore is useful for intermediate raw materials for wiring base plate, photosensitive and liquid crystal materials. Such a structure is that all C—H bonds in the phthalic anhydride portions in both sides of the dianhydride are substituted with C—F bonds, and all C—H group in the benzene ring in the central portion thereof substituted with C-other halogen atom groups than F, partially including C—F group. Based on the above knowledge, we have completed the present invention.

The present invention relates to a new halogen-containing aromatic acid dianhydride represented by the formula 1 (hereinafter it is referred to as "HAA").

In the formula 1, X is a chlorine, bromine or iodine atom, preferably chlorine or bromine atom, and most preferably chlorine atom. The term m indicates the bonding number of X to the benzene ring, an integer of 1 to 4, preferably an integer of 2 to 4, and most preferably 4. The term n indicates the bonding number of fluorine atom to the benzene ring, an integer of 3 to 0, preferably an integer of 2 to 0, and most preferably 0. In the formula 1, the sum of n and m is 4.

The HAA preferably includes a compound represented by the formula:

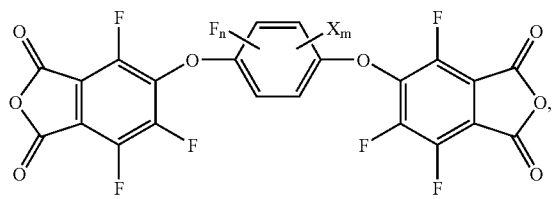

more preferably 1,4-bis(3,4-dicarboxytrifluorophenoxy)tetrachlorobenzene dianhydride, 1,4-bis(3,4-dicarboxytrifluorophenoxy)tetrabromobenzene dianhydride, 1,4-bis(3,4-dicarboxytrifluorophenoxy)-2-chlorotrifluoro benzene dianhydride, 1,4-bis(3,4-dicarboxytrifluorophenoxy)-2-bromotrifluorob enzene dianhydride, and most preferably 1,4-bis(3,4-dicarboxytrifluorophenoxy)tetrachlorobenzene dianhydride.

The HAA is represented by a combination of p-phenyldioxy group represented by the formula:

with trifluorophenyl group represented by the formula:

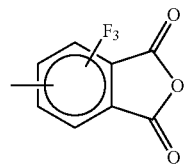

The HAA can be produced in a combination of known methods. The production method of 1,4-bis(3,4-dicarboxytrifluorophenoxy)tetrachlorobenzene dianhydride as the representative will be explained below. Other HAAs of the present invention can be produced in the similar manner as the above, using, in tetrachlorohydroquinone (or its metal salts such as 2 Na salt), the corresponding halogen atom instead of the chlorine atom.

The objective 1,4-bis(3,4-dicarboxytrifluorophenoxy)tetrachlorobenzene dianhydride is produced as an embodiment by reacting tetrafluorophthalonitrile and tetrachlorohydroquinone (or its metal salts such as 2 Na salt; it is summarized as "tetrachlorohydroquinone") in the presence of a base in a solvent at a temperature of −20° C. to 200° C. for 0.1 to 20 hours to form 1,4-bis(3,4-dicyanotrifluorophenoxy)tetrachlorobenzene (Step 1a); hydrolyzing the resulting 1,4-bis(3,4-dicyanotrifluorophenoxy)tetrachlorobenzene with an acid at a temperature of 50° C. to 300° C. for 0.5 to 20 hours to form 1,4-bis(3,4-dicarboxytrifluorophenoxy)tetrachlorobenzene (Step 1b); dissolving the reaction solution including 1,4-bis(3,4-dicarboxytrifluorophenoxy)tetrachlorobenzene in a medium containing an organic solvent once, purifying and separating the product therefrom (Step 1c); and then dehydrating the separated 1,4-bis(3,4-dicarboxytrifluorophenoxy)tetrachlorobenzene (Step 1d).

Now each step will be explained in turn.

As the base to be used in Step 1a, there can be cited an alkali metal salt, such as potassium fluoride, sodium fluoride, lithium fluoride, potassium chloride, sodium chloride and lithium chloride; an alkali earth metal salt such as calcium chloride and magnesium chloride; a carbonate of alkali metals such as sodium hydrogen carbonate, lithium hydrogen carbonate, potassium hydrogen carbonate, sodium carbonate, lithium carbonate and potassium carbonate; a carbonate of alkali earth metals such as calcium carbonate and magnesium carbonate; a tertiary amine such as trimethylamine, triethylamine, tripropylamine, tributylamine, tricyclohexylamine, tribenzylamine, triphenylamine and pyridine, and preferably potassium fluoride, sodium carbonate, potassium carbonate, triethylamine, tripropylamine and pyridine. The base can be added in order to effectively proceed with the reaction of tetrafluorophthalonitrile and tetrachlorohydroquinone. The base is added usually in the range of 0.5 to 20 mol %, preferably 2 to 10 mol %, based on the amount of tetrachlorohydroquinone.

As the solvent to be used in Step 1a, there can be cited nitriles such as acetonitrile and benzonitrile; ketones such as methylisobutylketone (MIBK), methylethylketone (MEK) and cyclohexanone; halogenated hydrocarbons such as chloroform, methylene chloride, carbon tetrachloride, chloroethane and di-, tri- and tetra-chloroethane; aromatic hydrocarbons such as benzene, toluene and xylene; hydrocarbons such as pentane, hexane, cyclohexane and heptane; ethers such as diethylether, isopropylether, tetrahydrofuran (THF), dioxane, diphenylether, benzylether and tert-butylether; esters such as methyl formate, ethyl formate, methyl acetate, ethyl acetate, propyl acetate, and isopropyl acetate; N-methylpyrrolidinone (NMP), dimethylformamide (DMF), dimethylsulfoxide (DMSO) and dimethylacetamide, and preferably acetonitrile, MIBK, NMP, DMF and DMSO. The solvent can be added in order to effectively proceed with the reaction. For instance, tetrafluorophthalonitrile may be in the range of 1 to 80% by weight, and preferably 5 to 50% by weight, based on the weight of the solvent.

The mixing ratio of tetrafluorophthalonitrile to tetrachlorohydroquinone is stoichiometrically 2:1 (molar ratio). The mixing ratio may be usually by molar ratio in the range of 2:1 to 100:1, and preferably 2:1 to 50:1 in view of reaction efficiency and reaction selectivity.

As the acid to be used in Step 1b, there can be cited sulfuric acid, hydrochloric acid, phosphoric acid or oxalic acid in the form of as it is or an aqueous solution (acid solution). In the case of the acid solution, it is necessary to fully hydrolyze 1,4-bis(3,4-dicyanotrifluorophenoxy)tetrachlorobenzene. The acid concentration may be in the range of 0.40 to 85% by weight depending on reaction temperatures, and kinds of acids. In the case of sulfuric acid, the acid concentration in aqueous sulfuric acid solution is preferably in the range of 50 to 80% by weight. The acid can be added to fully hydrolyzing 1,4-bis(3,4-dicyanotrifluorophenoxy) tetrachlorobenzene. The concentration of 1,4-bis(3,4-dicyanotrifluorophenoxy)tetrachlorobenzene to the acid to be added may be usually in the range of 1 to 60% by weight, and preferably in the range of 5 to 50% by weight depending on reaction temperatures and kinds of acids.

As concrete examples for Step 1c, there can be cited a method in which to the resulting product in Step 1b are poured an organic solvent of capable of forming two layers with the water to dissolve the product into the organic solvent, and then the organic layer is separated, evaporated to dryness. By this method, phthalamide derivatives into which 1,4-bis(3,4-dicarboxytrifluorophenoxy)tetrachlorobenzene has been incorporated, can be deposited on the surface of solids. Suitable organic solvents should form a two-layer state with water, and not react the products, but for example include fatty acid esters, ketones, ethers, and benzonitriles, more preferably fatty acid esters and ketones, and most preferably ethyl acetate, isopropyl acetate, methylisobutylketone. The solvent can be added to effectively dissolve the products or more. Then, the organic layer is separated from the solution, and may be washed with water if necessary.

As other examples for Step 1c, there can be cited methods; in Step 1b, to 1,4-bis(3,4-dicarboxytrifluorophenoxy) tetrachlorobenzene as the residue, are poured an organic solvent and water to dissolve the residue into the organic solvent, the organic layer is separated if the organic solvent forms a two-layer state with water, and then evaporated to dryness to produce an objective material; alternatively if the organic solvent added and water do not form a two-layer state, filtration is performed till solids precipitate by adding water, followed by drying thereby producing an objective product. In this case, organic solvents that form a two-layer state, are the same as the above solvent. Organic solvents should not form a two-layer state, and not react the products, but for example include ketones such as acetone, acetonitriles such as acetonitrile, and alcohols such as methanol and ethanol, and preferably ketons. Otherwise, the organic solvents that do not form a two-layer state should be added to effectively dissolve the products or more. Then, water is added to precipitate solids, the resulting solid is filtrated, dried to obtain a product. In this case, water should be added to effectively precipitate the solid or more, and may be five times in weight if the organic solvent is acetone.

In the first embodiment, Steps 1b and 1c are performed at least one. If these steps are repeated, it is preferably performed in the state of combination of Steps 1b and 1c, but Step 1b or Step 1c may be independently repeated if necessary. Suitable repeating numbers comprise usually 2 to 10 times, and preferably 3 to 6 times. In this case, Steps 1b and 1c may be performed in the same or different conditions.

In Step 1d, dehydration may be performed according to known methods: (1) dehydration is performed at 0° C. to 200° C. for 0.5 to 50 hours in dehydration agents such as thionyl chloride, sulfuric acid, concentrated sulfuric acid, phosphoric acid, metaphosphoric acid, polyphosphoric acid, anhydrous hydrofluoric acid, $P_2O_5$, sodium hydrogen sulfate, anhydrous zinc chloride, phosphorus oxychloride, acetic anhydride, acetyl chloride, oxalic acid, sulfonic acid and phthalic anhydride; (2) a gas phase catalytic reaction is performed using dehydration catalysts such as alumina catalysts, phosphoric acid or phosphate, which is deposited on inert carriers such as diatomaceous earth, silica-alumina catalysts and activated clay; (3) heating is performed at a temperature of 150° C. to 300° C. in the state of non-aqueous solution or solid state. Among them, the above (1) is prefer in which dehydration is performed at a temperature of 50° C. to 200° C. for 0.1 to 20 hours in the dehydration agents such as thionyl chloride, phosphoric acid, polyphosphoric acid, acetic anhydride and phthalic anhydride.

Alternatively, in the first embodiment, the objective 1,4-bis(3,4-dicarboxytrifluorophenoxy)tetrachlorobenzene dianhydride can be directly synthesized by simultaneous hydrolysis and dehydration by heating 1,4-bis(3,4-dicyanotrifluorophenoxy)tetrachlorobenzene in an acid at 100° C. to 300° C. for 5 to 40 hours. In this case, the acid may be cited as the same as the above.

On the other hand, the objective 1,4-bis(3,4-dicarboxytrifluorophenoxy)tetrachlorobenzene dianhydride can be produced in accordance with the method described in JP-A-9-110,784. To put it simply, the objective is produced in a highly pure and yields by in the same manner as the first embodiment, synthesizing 1,4-bis(3,4-dicyanotrifluorophenoxy)tetrachlorobenzene (Step 1a'), heating the resultant in an acid or aqueous acidic medium to form a product including 1,4-bis(3,4-dicarboxytrifluorophenoxy)tetrachlorobenzene (Step 1b'), adding an alkaline substance to the reaction solution to be alkaline and heating (Step 1c'), then adding an acidic substance into this alkaline product solution to be acidic to separate 1,4-bis(3,4-dicarboxytrifluorophenoxy) tetrachlorobenzene in high pure (Step 1d'), and dehydrating the product (Step 1e').

The HAA has a relatively high melting point, and low solubility into dimethylacetoamide, thus excels in heat resistance and chemical resistance.

In accordance with the present invention, since HAA excels in heat resistance, chemical resistance, water repellent property and low dielectric property, it is expected to be useful for intermediate materials for wiring base plate, photosensitive and liquid crystal materials.

(HTC)

In a first aspect, the present invention relates to a new halogen-containing aromatic tetranitrile compound represented by the formula 21 (hereinafter it is referred to as "HTC").

In the formula 21, X is a chlorine, bromine or iodine atom, preferably chlorine or bromine atom, and most preferably chlorine atom. The term m indicates the bonding number of X to the central benzene ring without cyano groups, an integer of 1 to 4, preferably an integer of 2 to 4, and most preferably 4. The term n indicates the bonding number of fluorine atom to the central benzene ring without cyano groups, an integer of 3 to 0, preferably an integer of 2 to 0, and most preferably 0. In the formula 21, the sum of n and m is 4.

The HTC preferably includes a compound represented by the formula:

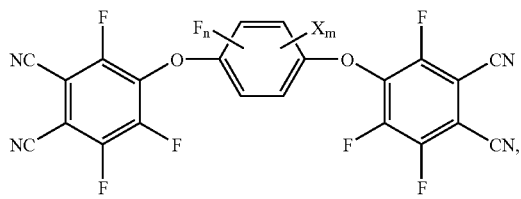

more preferably 1,4-bis(3,4-dicyanotrifluorophenoxy)tetrachlorobenzene, 1,4-bis(3,4-dicyanotrifluorophenoxy)tetrabromobenzene, 1,4-bis(3,4-dicyanotrifluorophenoxy)-2-chlorotrifluorobe nzene, and 1,4-bis(3,4-dicyanotrifluorophenoxy)-2-bromotrifluoroben zene, and most preferably 1,4-bis(3,4-dicyanotrifluorophenoxy)tetrachlorobenzene.

The HTC is represented as the combination of p-phenyldioxy group represented by the formula:

and dicyanotrifluorophenyl group represented by the formula:

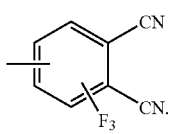

The HTC can be produced in a combination of known methods, preferably by the reaction of tetrafluorophthalonitrile and a hydroquinone derivative represented by the formula 23. In a second aspect, the present invention relates to a method for producing a HTC by means of the reaction of tetrafluorophthalonitrile with a hydroquinone derivative represented by the formula 23 (hereinafter it may be referred to as "hydroquinone derivative"). In the formula 23, X, m, and n mean the same as those in the formula 21.

Hydroquinone derivatives to be used in the second aspect, may be appropriately selected, depending on the kinds of the HTC, preferably from tetrachlorohydroquinone, tetrabromohydroquinone, 2-chloro-3,5,6-trifluorohydroquinone, 2-bromo-3,5,6-trifluorohydroquinone, or metal salts such as 2 sodium salt and 2 potassium salt, and most preferably tetrachlorohydroquinone and its 2 sodium salt. The hydroquinone derivative may be theoretically used in one mole based on two moles of tetrafluorophthalonitrile as the other raw material. In consideration of reaction efficiency and reaction selectivity, excess tetrafluorophthalonitrile should be preferably present. Concretely, the hydroquinone derivative may be preferably in the range of 1 to 50 moles, and more preferably in the range of 2 to 50 moles, per 100 moles of tetrafluorophthalonitrile.

In the second aspect, the reaction of tetrafluorophthalonitrile and the hydroquinone derivative is preferably performed in the presence of a base, in consideration of reaction efficiency. In this case, suitable bases include an alkali metal salt such as potassium fluoride, sodium fluoride, lithium fluoride, potassium chloride, sodium chloride, and lithium chloride; an alkaline earth metal salt such as calcium chloride and magnesium chloride; a carbonate of alkali metals such as sodium hydrogen carbonate, lithium hydrogen carbonate, potassium hydrogen carbonate, sodium carbonate, lithium carbonate and potassium carbonate; a carbonate of alkaline earth metals such as calcium carbonate and magnesium carbonate; a tertiary amine such as trimethylamine, triethylamine, tripropylamine, tributylamine, tricyclohexylamine, tribenzylamine, triphenylamine, and pyridine; and preferably potassium fluoride, sodium carbonate, potassium carbonate, triethylamine, tripropylamine and pyridine. The base may be added in order to effectively proceed with the reaction of tetrafluorophthalonitrile and the hydroquinone derivative, but for example usually in the range of 0.5 to 20 mol %, and preferably in the range of 2 to 10 mol %, based on the amount of the hydroquinone derivative.

Further, in the second aspect, the reaction of tetrafluorophthalonitrile and the hydroquinone derivative may be performed in the presence or absence of a solvent. Suitable solvents include nitrites such as acetonitrile and benzonitrile; ketones such as acetone, methylisobutylketone (MIBK), methylethylketone (MEK) and cyclohexanone; halogenated hydrocarbons such as chloroform, methylene chloride, carbon tetrachloride, chloroethane and di-, tri- and tetra-chloroethane; aromatic hydrocarbons such as benzene toluene and xylene; hydrocarbons such as pentane, hexane, cyclohexane and heptane; ethers such as diethylether, isopropylether, tetrahydrofuran (THF), dioxane, diphenylether, benzylether and tert-butylether; esters such as methyl formate, ethyl formate, methyl acetate, ethyl acetate, propyl acetate and isopropyl acetate, N-methylpyrrolidinone (NMP), dimethylformamide (DMF), dimethylsulfoxide (DMSO) and dimethylacetamide, and preferably acetonitrile, MIBK, NMP, DMF and DMSO. The solvent may be added in order to effectively proceed with the reaction, but usually in such a way that tetrafluorophthalonitrile is in the range of 1 to 80% by weight, and preferably in the range of 5 to 50% by weight, based on the weight of the solvent.

In the second aspect, the reaction condition of tetrafluorophthalonitrile and the hydroquinone derivative may be appropriately selected so as to proceed with the reaction effectively, but for example suitable reaction temperatures are usually in the range of −50° C. to 300° C., and preferably in the range of −20° C. to 200° C., and suitable reaction times usually in the range of 0.1 to 40 hours, and preferably 0.1 to 20 hours. The reaction may be performed in the conditions of a reduced, normal or compressed pressure, and preferably normal pressure in view of equipment.

In the second aspect, hydrogen fluoride generated by the reaction of tetrafluorophthalonitrile and the hydroquinone derivative may be preferably removed by conventional methods: after reaction, the HTC is extracted with a non-aqueous organic solvent, and then washed with water; and in advance, a base is added into the reaction system to trap the hydrogen fluoride as the salt. Suitable non-aqueous organic solvents in the first method, include ketones such as MIBK, MEK and cyclohexanone; halogenated hydrocarbons such as chloroform, methylene chloride, carbon tetrachloride, chloroethane and di-, tri- and tetra-chloroethane; aromatic hydrocarbons such as benzene, toluene and xylene; hydrocarbons such as pentane, hexane, cyclohexane and heptane; ethers such as diethylether, isopropylether, diphenylether, benzylether, tert-butylether; esters such as methyl formate ethyl formate, methyl acetate, ethyl acetate, propyl acetate, isopropyl acetate, and preferably MIBK, MEK and isopropylether and ethyl acetate. In the second method, suitable bases include a calcium compound such as calcium chloride and calcium carbonate; a tertiary amine such as trimethylamine, triethylamine, tripropylamine, tributylamine, tricyclohexylamine, tribenzylamine, triphenylamine and pyridine, and preferably calcium compounds. When calcium compounds are used, it can react with hydrogen fluoride to form calcium fluoride ($CaF_2$) as precipitates, which can be readily removed for example by filtration.

In a third aspect, the present invention relates to a new halogen-containing aromatic tetracarboxylic acid represented by the formula 22 (hereinafter it is referred to as "HTA"). The HTA is represented, in the same manner as the first aspect, as a combination of p-phenyldioxy group represented by the above formula with dicarboxytrifluorophenyl group represented by the formula:

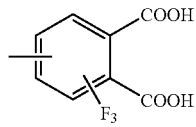

In the formula 22, X, m and n are the same as those defined in formula 21.

Suitable HTAs include a compound represented by the formula:

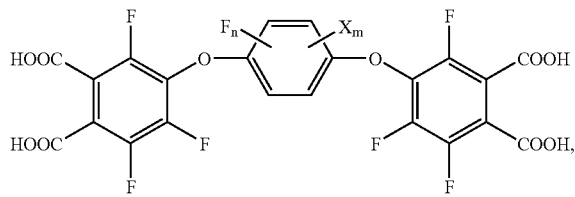

preferably 1,4-bis(3,4-dicarboxytrifluorophenoxy)tetrachlorobenzene, 1,4-bis(3,4-dicarboxytrifluorophenoxy)tetrabromobenzene, 1,4-bis(3,4-dicarboxytrifluorophenoxy)-2-chlorotrifluoro benzene, and 1,4-bis(3,4-dicarboxytrifluorophenoxy)-2-bromotrifluorob enzene, and most preferably 1,4-bis(3,4-dicarboxytrifluorophenoxy)tetrachlorobenzene.

The HTA of the present invention can be produced by a combination of known methods, preferably by hydrolyzing the HTC of the first aspect of the present invention. In accordance with a fourth aspect of the present invention, it relates to a method for producing HTA as the third aspect of the present invention by hydrolyzing the HTC as the first aspect of the present invention.

In the fourth aspect, the HTC may be hydrolyzed preferably in the presence of an acid, and more preferably in the presence of the acid in an organic solvent. Suitable acids include sulfuric acid, hydrochloric acid, phosphoric acid and oxalic acid in the form of acid itself or an aqueous solution. In the case of the aqueous solution, the acid concentration should fully hydrolyze HTC, but be for example in the range of 40 to 85% by weight depending on the kinds of reaction temperatures and acids. Among them, sulfuric acid, in particular an aqueous 50 to 80% by weight sulfuric acid solution is preferable. The acid may be added so as to fully hydrolyze the HTC, but usually the concentration of HTC to the acid to be added may be in the range of 1 to 60% by weight, and preferably in the range of 5 to 50% by weight.

The organic solvent to be used in the fourth aspect, should dissolve HTC, but for example include-inorganic or organic acids. For example, it can be cited organic acids such as formic acid, acetic acid and propionic acid; acid anhydrides such as formic anhydride, acetic anhydride and propionic anhydride; nitriles such as acetonitrile and benzonitrile; ketones such as acetone, MIBK, MEK and cyclohexanone; halogenated hydrocarbons such as chloroform, methylene chloride, carbon tetrachloride, chloroethane and di-, tri- and tetra-chloroethane; aromatic hydrocarbons such as benzene, toluene and xylene; hydrocarbons such as pentane, hexane, cyclohexanone and heptane; ethers such as diethylether, isopropylether, THF, dioxane, diphenylether, benzylether and tert-butylether; esters such as methyl formate, ethyl formate, methyl acetate, ethyl acetate, propyl acetate and isopropyl acetate; NMP, DMF, DMSO and dimethylacetamide, preferably an organic acid and acid anhydride, and most preferably acetic acid, propionic acid, acetic anhydride and propionic anhydride. The organic solvent may be added so as to fully dissolve the HTC, but the concentration of the HTC is usually in the range of 1 to 60% by weight, and preferably in the range of 5 to 50% by weight, based on the weight of the organic solvent. In the present invention, the organic solvent may include water unless it blocks the dissolution of the HTC and the hydrolysis by acids.

In the fourth aspect, HTC, acids and organic solvents are arbitrarily mixed for example in a lump, the HTC is dissolved in the organic solvent, and then the acid is added therein; or the organic solvent and acid are mixed and then the HTC added therein. In order to effectively hydrolyze the HTC with the acid, it is preferred to dissolve the HTC into the organic solvent to form a uniform solution, and then to this solution is added the acid. In the conventional method for hydrolyzing the HTC using the acid alone, plural of hydrolysis steps using acids must be repeated so as to heighten the purity of the objective product, since the dissolving of the raw material into the aqueous acid solution is not sufficient, fully hydrolysis is not performed and thus the purity of the objective product is not fully improved. It is found that, when the HTC is dissolved in advance and then hydrolysis is performed by means of acids, a halogen-containing aromatic compound having a prescribed purity can be obtained at one time by means of hydrolysis by acids. In order to effectively hydrolyze the HTC with acids in the organic solvent, it is preferred to add the acids while stirring the tetranitrile solution.

In the present invention, suitable hydrolysis conditions of the HTC are fully hydrolyze the HTC for example that the hydrolysis temperature is preferably in the range of 20° C. to 300° C., and more-preferably in the range of 50° C. to 200° C., and the hydrolysis duration usually in the range of 0.1 to 40 hours, and preferably 0.5 to 20 hours.

One embodiment of the fourth aspect of the present invention has been explained as above, but the present method is not restricted to the above method. Now, another embodiment of the fourth aspect of the present invention will be explained below.

In accordance with another embodiment of the fourth aspect of the present invention, HTC is heated in an aqueous acidic medium to obtain a reactant solution including the corresponding HTA (Step 2a); to this reactant solution is added an alkali substance to alkali and heating is performed (Step 2b); and then to the alkali reactant solution is added an acidic substance to acidic, the objective HTA is separated from the solution (Step 2c). In accordance with this method, the objective HTA having a high purity can be produced.

Next, each step will be explained in turn.

In Step 2a, the HTC may be poured together with an aqueous acidic medium or into the aqueous acidic medium one by one. In the latter case, the HTC may be added in the form of powder as it is, or solutions of such as acetic anhydride, propionic anhydride and acetonitrile. Suitable aqueous acidic medium include an aqueous organic or inorganic solution of capable of changing cyano (—CN) group to carboxyl (—COOH) group, and preferably an aqueous solution of inorganic acids such as phosphorous acid, sulfuric acid and hydrochloric acid. Among them, an aqueous sulfuric acid solution, usually in the acid concentration of 40 to 85% by weight, and preferably in the acid concentration of 50 to 80% by weight, is preferable in view of high yields. The HTC may be added so as to produce the objective product in a high yield, but preferably in the range of 5 to 50% by weight, based on the weight of the aqueous acidic medium. Suitable reaction conditions in accordance with the embodiment of the present invention are to produce the objective product in a high yield, but suitable reaction temperatures are in the range of 120° C. to 180° C., and preferably in the range of 140° C. to 170° C., and suitable reaction durations are usually in the range of 1 to 24 hours depending on the reaction temperature. After the completion of reaction, the HTA is precipitated in the reactant solution, and the reactant solution may be used as it is or after separation, residues may be used.

In Step 2b, in using the reactant solution containing the HTA as it is, to the reactant solution is added an alkali substance in the form of solid, vapor or an aqueous solution. On the other hand, in using the HTA as the residue, to the residue is added water if necessary, and then added an alkali substance in the form of solid, vapor or an aqueous solution. Suitable alkali substances include a hydroxide of alkali metals such as sodium hydroxide and potassium hydroxide; a carbonate of alkali metals such as sodium carbonate and potassium carbonate; a bicarbonate of alkali metals such as sodium bicarbonate and potassium bicarbonate; a hydroxide of alkaline earth metals such as magnesium hydroxide, calcium hydroxide, strontium hydroxide and barium hydroxide; a carbonate of alkaline earth metals such as magnesium carbonate, calcium carbonate, strontium carbonate and barium carbonate; a bicarbonate of alkaline earth metals such as magnesium bicarbonate, calcium bicarbonate, strontium bicarbonate and barium bicarbonate; and ammonia, preferably a hydroxide of alkali metals, a carbonate of alkali metals, a bicarbonate of alkali metals, and most preferably a hydroxide of alkali metals. The alkali substance may be added singly or in a combination thereof. The alkali substance may be added so as to obtain the objective product in a high yield, but preferably adjust the pH of the reaction solution in the range of 9.5 to 12.5, and more preferably in the range of 11.0 to 12.0. The amount of the alkali substance in the case of adjusting the pH corresponds to preferably the sum of the amount of the alkali substance to neutralize the acid in the aqueous acidic medium used in Step 2a, and the amount of the alkali substance in the range of 3.5 to 4.5 mol, and preferably 3.8 to 4.2 mol as monovalent based on the HTA used in the reaction. Suitable reaction conditions are appropriately selected so as to obtain the objective product in efficiently and having a high yield, but suitable temperatures are usually in the range of 30° C. to 150° C., and preferably in the range of 70° C. to 130° C., suitable reaction durations are usually less than 8 hours, and preferably in the range of 1 to 6 hours.

In Step 2c, an acidic substance may be added so as to acidify the reactant solution, but for example include an organic or inorganic acid, and preferably an inorganic acid such as sulfuric acid, hydrochloric acid and phosphoric acid. Suitable acidic substance may be added as it is or may be added in the form of solutions using water or the like, but include more preferably in the form of an aqueous sulfuric acid solution. The sulfuric acid concentration in the aqueous solution is preferably in the range of 1 to 50% by weight. Suitable acidic substances may be added so as to acidify the carboxyl groups neutralized by the alkali substance in Step 2b or more. Usually, the acidic substance may be added to acidify the corresponding alkali substance amount, which is obtained by reducing the amount necessary to be neutralized with the acid from the total alkali amount used in Step 2b, or more. The acidic substance may be added into the alkali reactant solution in a singly or sequentially.

After addition of the acidic substance, if the objective tetracarboxylic acid salt is a salt, which is easily dissolved into water, such as sodium sulfate, potassium sulfate, ammonium sulfate and sodium chloride, the salt can be separated readily by filtration, extraction or the like. If the salt of the objective product, after addition of the acidic substance, is a salt, which is difficult to dissolve in water, the salt can be separated by means of extraction or the like. In the case of filtration, after filtration the residue is washed with an appropriate amount of water to preferably remove the acidic substance added and the salt formed. In the case of extraction, after dissolving the objective product with a suitable solvent, the objective product is separated by separating the solution therefrom in that the resulting salt is a solution, or by filtrating and separating the solution in that the resulting salt is precipitated. After separating the solution, the product is preferably washed with an approximate amount of water to remove the acid added and the salt formed in view of purity of the objective product. Suitable solvents to be used in this case should form a two-layer state and further dissolve the objective product, but for example include fatty acid esters, ketones, ethers and benzonitriles, and more preferably fatty acid esters and ketons. Concretely, ethyl acetate, isopropyl acetate, methylisopropylketone or methylisobutylketone is preferable.

In accordance with other embodiments of the fourth aspect, HTC is heated in an acidic medium to obtain a reactant solution containing the corresponding HTA (Step 2a); then this reactant solution is dissolved in a medium containing organic solvents once and the product is separated from the medium (Step 2b'); at least two of Steps 2a to 2b' to separate the HTA from the reactant solution (Step 2c). In accordance with this method, the objective HTA can be obtained in a high purity. In this embodiment, Step 2a is the same as the above.

As an concrete example for Step 2b', there can be cited a method for precipitating on the surface of solids a phthalamide derivative incorporated into the HTA by adding an organic solvent into the reactant solution produced in Step 2a to form a two-layer state, dissolving the product into the organic solvent, then separating the solution, and then evaporating the solution to dryness. Suitable organic solvents form a two-layer state with water, and do not react with the product, but for instance include fatty acid esters, ketones, ethers and benzonitriles, and preferably fatty acid esters and ketones. For example, ethyl acetate, isopropyl acetate or methylisobutylketone are preferable. The organic solvent is used to dissolve the product or more. Subsequently, the organic layer is separated from the medium and washed with water if necessary.

In using the HTA in Step 2a as the residue, to the residue are added an organic solvent and water to dissolve the residue into the organic solvent. If the organic layer forms a two-layer state, the organic layer is separated and evaporated to dryness, thereby obtaining the objective product; or if the organic solvent added does not form a two-layer state, water is added till solids precipitate, the precipitate is filtrated and dried to dryness. In this case, the organic solvent which form a two-layer state, is the same as the above. The organic solvent which does not form a two-layer state, should does not react with the product, but for example include ketones such as acetone; acetonitriles such as acetonitrile; alcohols such as methanol and ethanol, and preferably ketons. The organic solvent which does not form a two-layer state with water is added to dissolve the product or more. Subsequently, water is added till solids precipitate, and the product is obtained by filtration and dryness. Water is added to precipitate the solids or more, but for example five times or more at volume if the organic solvent is acetone.

Steps 2a to 2b' may be repeated more than two, usually 2 to 10 times, and preferably 3 to 6 times. Each step 2a and step 2b' may be same or not in each step.

The HTA thus obtained is dehydrated to produce the corresponding HAA. In accordance with a five aspect of the present invention, it can provides a method for producing a HAA represented by the formula 1 by dehydrating the HTA as the third aspect of the present invention.

In the fifth aspect, HTA can be dehydrated in known methods, for example (21) dehydration is performed at 0° C. to 200° C. for 0.5 to 50 hours in dehydration agents such as thionyl chloride, sulfuric acid, concentrated sulfuric acid, phosphoric acid, metaphosphoric acid, polyphosphoric acid, anhydrous hydrofluoric acid, $P_2O_5$, sodium hydrogen sulfate, anhydrous zinc chloride, phosphorus oxychloride, acetic anhydride, acetyl chloride, oxalic acid, sulfonic acid and phthalic anhydride; (22) a gas phase catalytic reaction is performed using dehydration catalysts such as alumina catalysts, phosphoric acid or phosphate, which is deposited on inert carriers such as diatomaceous earth, silica-alumina catalysts and activated clay; (23) heating is performed at a temperature of 150° C. to 300° C. in the state of non-aqueous solution or solid state. Among them, the above (21) is prefer in which dehydration is performed at a temperature of 50° C. to 200° C. for 0.1 to 20 hours in the dehydration agents such as thionyl chloride, phosphoric acid, polyphosphoric acid, acetic anhydride and phthalic anhydride.

The objective halogen-containing aromatic tetracarboxylic acid dianhydride can be directly synthesized by heating 1,4-bis(3,4-dicyanotrifluorophenoxy)tetrachlorobenzene at a temperature range of 100° C. to 300° C. for 0.5 to 40 hours by performing hydrolysis and dehydration at the same time. The HTA and HTC are useful for the raw materials of the corresponding HAA.

(HPC)

The present invention provides a halogenated m-phenylenediamine compound represented by the formula 31 (hereinafter it is referred to as "HPC"):

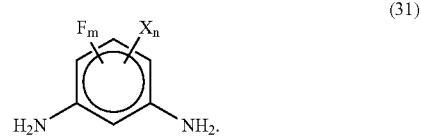

In the formula 31, X is a chlorine or bromine atom, may be identical or different from each other if X is present in a state of plural (namely n is 2 or 3), n indicates the bonding number of X to the benzene ring, an integer of 1 to 3, preferably an integer of 1 or 2, and most preferably 1. The position of X to the benzene ring depends on the bonding number and kinds of X, and a prescribed property of fluorine-containing compounds, but is preferably 4 or 5 if n is one, and 4 and 6 if n is two.

Further, in the formula 31, m indicates the bonding number of fluorine atom to the benzene ring, an integer of 3 to 1, preferably an integer of 3 or 2, and most preferably an integer of 3. The sum of n and m is 4 in the formula 31. In other words, the halogenated m-phenylenediamine has a compound without carbon-hydrogen bonds.

Suitable halogenated m-phenylenediamine compound of the present invention preferably include 4-bromo-2,5,6-trifluoro-m-phenylenediamine, 4-chloro-2,5,6-trifluoro-m-phenylenediamine, 5-bromo-2,4,6-trifluoro-m-phenylenediamine, 5-chloro-2,4,6-trifluoro-m-phenylenediamine, 4,6-dibromo-2,5-difluoro-m-phenylenediamine, and 4,6-dichloro-2,5-difluoro-m-phenylenediamine, more preferably 4-bromo-2,5,6-trifluoro-m-phenylenediamine, 4-chloro-2,5, 6-trifluoro-m-phenylenediamine, 5-chloro-2,4,6-trifluoro-m-phenylenediamine, and 5-bromo-2,4,6-trifluoro-m-phenylenediamine.

The HPC of the present invention can be produced by applying a known method as follows.

In accordance with an embodiment, the objective HPC can be produced by forming halogenated trifluoroisophthalonitrile (3a); forming a halogenated trifluoroisophthalic acid from the halogenated trifluoroisophthalonitrile (3b); reacting this halogenated trifluoroisophthalic acid with an azide compound in the presence of a Lewis base in a solvent to form an acid azide, thermal rearranging and hydrolyzing this acid azide (3c). In this specification, the term "halogenated trifluoroisophthalonitrile" means a compound in which both —$NH_2$ groups in the HPC of the present invention are substituted with —CN groups, and the term "halogenated trifluoroisophthalic acid" means a compound in which both —$NH_2$ groups in the HPC thereof are substituted with —COOH groups.

Step 3a in an embodiment of the HPC of the present invention will be explained as follows.

Halogenated trifluoroisophthalonitrile is produced in a known method, for example the method described in JP-B-63-5023.

A first embodiment for producing a halogenated trifluoroisophthalonitrile of the present invention will be explained below. In accordance with the first embodiment, tetrafluoroisophthalonitrile is reacted with a brominating or chlorinating agent (hereinafter it may be referred to as "halogenating agent".) to replace the fluorine atoms bonded to the benzene ring with bromine or chlorine atom. For example, by specifically substituting the fluorine at the 4-position in tetrafluoroisophthalonitrile, 4-bromo-2,5,6-trifluoroisophthalonitrile or 4-chloro-2,5,6-trifluoroisophthalonitrile can be obtained in a high yield.

In the first embodiment, suitable brominating agents include known brominating agents, but for example sodium bromide, potassium bromide and lithium bromide. Sodium bromide and potassium bromide are preferable in view of readily handling and availability.

In the first embodiment, suitable chlorinating agents include known chlorinating agents, but for example sodium chloride, potassium chloride and lithium chloride. Sodium chloride and potassium chloride are preferable in view of readily handling and availability.

In the first embodiment, the halogenating agent may be added to specifically substitute the fluorine atom at the 4-position in tetrafluoroisophthalonitrile with bromine or chlorine atom or more, but for example in the range of 1 to 5 moles, and preferably in the range of 1 to 2 moles, per mol of tetrafluoroisophthalonitrile. If it exceeds 5 moles, there is a fear that fluorine atoms except for the 4-position in tetrafluoroisophthalonitrile will be substituted with bromine or chlorine atom, and further it is necessary to treat the remaining halogenating agent, and therefore not economically. In contrast, if it is less than 1 mole, the fluorine atom in the 4-position will not be fully substituted with such an agent, and unreacted raw material will remain in a large amount.

In the first embodiment, the bromination or chlorination of tetrafluoroisophthalonitrile may be performed in the presence or absence of a solvent, but preferably in the presence of the solvent. Suitable solvents include those which do not block such a bromination or chlorination, and are inert for the brominating or chlorinating agent, but for example nitriles such as acetonitrile and benzonitrile; ketones such as acetone, methylisobutylketone (MIBK), methylethylketone (MEK) and cyclohexanone; halogenated hydrocarbons such as chloroform, methylene chloride, carbon tetrachloride, chloroethane and di-, tri- and tetra-chloroethane; aromatic hydrocarbons such as benzene, toluene and xylene; hydrocarbons such as pentane, hexane, cyclohexane and heptane; ethers such as diethylether, isopropylether, tetrahydrofuran (THF), dioxane, diphenylether, benzylether and tert-butylether; esters such as methyl formate, ethyl formate, methyl acetate, ethyl acetate, propyl acetate and isopropyl acetate; N-methylpyrrolidinone (NMP), dimethylformamide (DMF), dimethylsulfoxide (DMSO), dimethylacetamide, sulfolan (TMSO$_2$) and dimethylsulfolan (DMSO$_2$); and more preferably acetonitrile, MIBK, NMP, DMF and DMSO. The solvent may be used in such a way that the concentration of tetrafluoroisophthalonitrile in the solvent is usually in the range of 2 to 80 (w/v)%, and more preferably in the range of 5 to 50 (w/v)%. The chlorination or bromination reaction may be performed preferably free from water so as to improve reaction velocity and prevent side reactions. In using solvents having a high hygroscopic property such as dimethylsulfoxide, sulfolan, dimethylformamide, N-methyl pyrrolidinone and dimethylsulfolan, benzene or toluene is added therein preferably so as to remove the water therefrom prior to the substitution reaction.

Tetrafluoroisophthalonitrile and the halogenating agent are reacted to fully proceed with the halogen substitution reaction, but the reaction temperature is usually in the range of 0° C. to 300° C., and preferably in the range of 50° C. to 250° C., and the reaction duration is usually in the range of 0.5 to 20 hours. The reaction may be performed under a reduced, normal or a compressed pressure, and preferably at normal pressure.

In a second embodiment, a halogenated trifluoroisophthalonitrile may be produced by fluorinating tetrachloroisophthalonitrile or tetrabromoisophthalonitrile (it may be referred to as "halogenated isophthalonitrile".) with a fluorinating agent. The chlorine or bromine atoms in the 2, 4, and 6 positions in halogenated isophthalonitrile are specifically substituted with fluorine atoms by means of nucleophilic substitution reaction to form a desired 5-chloro-2,4,6-trifluoroisophthalonitrile or 5-bromo-2,4,6-trifluoroisophthalonitrile in a high yield.

In the second embodiment, suitable fluorinating agents include known fluorinating agents, but for example potassium fluoride, cesium fluoride, sodium fluoride, barium fluoride, calcium fluoride and antimony fluoride, and preferably potassium fluoride in view of handling property and acquisition with ease.

The fluorinating agent may be added to specifically fluorinate the chlorine or bromine atoms in the 2,4,6 positions in halogenated isophthalonitrile, but stoichiometrically three times per mole of the raw material. Concretely, the fluorinating agent is usually in the range of 3 to 20 moles, and preferably 3 to 10 moles, per mole of halogenated isophthalonitrile. If it exceeds 20 moles, there is a fear that the 5-position will be fluorinated, and further it is necessary to treat the remaining fluorinating agents, so that not economical. In contrast, if it is less than 3 moles, the chlorine or bromine atoms in the 2,4,6 positions are not fully fluorinated, thereby the yield of the objective product will be lowered.

The fluorinating reaction for halogenated isophthalonitrile may be performed in the presence or absence of a solvent, but preferably in the presence of the solvent. Suitable solvents include those which do not block the fluorinating reaction and are inert for tetrachloroisophthalonitrile, tetrabromoisophthalonitrile and the fluorinating agents, but for example benzonitrile, DMSO, sulfolan (TMSO$_2$), DMF, N-methylpyrrolidinone (NMP), dimethylsulfolan (DMSO$_2$), acetonitrile, acetone, MEK and MIBK, and preferably benzonitrile and acetonitrile. The solvent may be used in such a way that the concentration of halogenated isophthalonitrile is usually in the range of 1 to 80 (w/v) %, and preferably 5 to 50 (w/v) %. The fluorination is preferably performed free from water so as to increase reaction velocity and prevent side reactions. For this purpose, in using solvents having a high hygroscopic property such as dimethylsulfoxide, sulfolan, dimethylformamide, N-methyl pyrrolidinone and dimethylsulfolan, benzene or toluene is added therein preferably so as to remove the water therefrom prior to the substitution reaction.

Halogenated isophthalonitrile and the fluorinating agent are reacted to fully proceed with the fluorination. The reaction temperature is usually in the range of 50° C. to 400° C., and preferably in the range of 100° C. to 300° C. The reaction duration is usually 0.5 to 20 hours. The reaction may be performed under a reduced, normal or a compressed pressure, but preferably either normal or a compressed pressure. In the case of compressed pressure, it is preferably in the range of 30 to 1000 kPa, and more preferably in the range of 100 to 800 kPa.

In the second embodiment, the fluorination may be performed in the presence of a phase-transfer catalyst so as to heighten the fluorination reaction velocity. Suitable phase-transfer catalysts include known phase-transfer catalysts, but for example crown compounds such as dibenzo-18-crown- 6-ether and polyethylene glycol: (molecular weight: 300 to 600). The catalyst may be added in the range of 0.1 to 10 moles, per mole of halogenated isophthalonitrile.

The halogenated trifluoroisophthalonitrile thus obtained can be purified by conventional purification methods, for example column chromatographs with silica gel or alumina, distillation preferably solid distillation, re-crystallization, re-precipitation and sublimation.

Step 3b in an embodiment for producing HPC of the present invention will be explained.

The halogenated trifluoroisophthalic acid can be produced by conventional methods, for example the halogenated trifluoroisophthalonitrile thus obtained is hydrolyzed to change the cyano groups to carboxyl groups. Alternatively, the halogenated trifluoroisophthalic acid can be also produced by halogenating compounds in which m-xylene, m-dialkyl benzene and the hydrogen atoms of these alkyl groups substituted with other atoms or an atomic group, and then oxidizing the alkyl groups, not depending Step 3a. Among them, the hydrolysis method is preferably cited, so that it will be explained below.

The hydrolysis of halogenated trifluoroisophthalonitrile is performed in the presence of an acid or base. Suitable acids include concentrated sulfuric acid, trichloroacetic acid, sulfuric acid, polyphosphoric acid such as pyrophosphoric acid, triphosphoric acid and tri- and tetra-methaphosphoric acids; trifluoroacetic acid, trifluoroacetic anhydride, hydrochloric acid, fuming sulfuric acid, concentrated hydrochloric acid, hydrobromic acid, propionic acid, formic acid, nitric acid, acetic acid; mixtures thereof for instance trifluoro acetic acid-trifluoroacetic anhydride (mixing ratio by weight: 1:9 to 9:1, preferably 3:7- to 7:3) and trichloroacetic acid-sulfuric acid (mixing ratio by weight: 1:9 to 9:1, preferably 3:7 to 7:3). The above acids may be used singly or in a combination thereof, and as it is or in the form of an aqueous solution. In the case of the solution, the concentration of acid in aqueous acid solution can be used to fully hydrolyze halogenated trifluoroisophthalonitrile or more, but for example in the range of 40 to 85% by weight, depending on the reaction temperature and kinds of the acid. Among them, sulfuric acid, in particular an aqueous 50 to 80% by weight of sulfuric acid is preferably used. Among them, at least one selected from the group consisting of polyphosphoric acid, trifluoroacetic acid-trifluoroacetic anhydride, trichloroacetic acid, propionic acid, hydrochloric acid, concentrated hydrochloric acid and sulfuric acid, in particular sulfuric acid, propionic acid, concentrated hydrochloric acid and polyphosphoric acid are preferably used. Suitable bases include sodium hydroxide, lithium hydroxide, potassium hydroxide, rubidium hydroxide, cesium hydroxide, beryllium hydroxide, magnesium hydroxide, calcium hydroxide, strontium hydroxide and barium hydroxide, and preferably sodium hydroxide, potassium hydroxide, calcium hydroxide and barium hydroxide. Also, the above base may be used singly or in a combination thereof. The acid or base is added to fully hydrolyze halogenated trifluoroisophthalonitrile, but for example the concentration of halogenated trifluoroisophthalonitrile to the acid or base to be added may be in the range of 1 to 80% by weight, and preferably in the range of 5 to 50% by weight.

Halogenated trifluoroisophthalonitrile should be fully hydrolyzed, but for instance the hydrolysis temperature is usually in the range of −20° C. to 200° C., preferably in the range of 0° C. to 150° C., and the its duration is usually in the range of 0.1 to 40 hours, and preferably in the range of 0.1 to 20 hours. The hydrolysis may be performed under a compressed, normal or a reduced pressure, but preferably normal pressure.

The halogenated trifluoroisophthalic acid thus obtained is purified by conventional purification methods, for example column chromatographs with silica gel or alumina, distillation preferably solid distillation, re-crystallization, re-precipitation and sublimation.

Step 3c in an embodiment for producing the above HPC will be explained below.

In Step 3c, the halogenated trifluoroisophthalic acid thus obtained in Step 3b is reacted with an azide compound in the presence of a Lewis base in a solvent to form an acid azide wherein the carboxyl groups in halogenated trifluoroisophthalic acid are changed to —$CON_3$ groups, and then this acid azide is thermally rearranged and hydrolyzed, thereby the objective HPC can be obtained.

Suitable azide compounds include a —$N_3$ groups, and change the carboxyl groups in halogenated trifluoroisophthalic acid to —$CON_3$ groups, but for example include a compound represented by the formula:

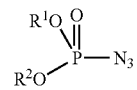

wherein $R^1$ and $R^2$ are independently alkyl groups having 1 to 5 carbon atoms, for instance methyl, ethyl, propyl, isopropyl, n-butyl, pentyl, neopentyl, sec-butyl and tert-butyl; cycloalkyl groups having 3 to 8 carbon atoms, for instance cyclopropyl, cyclobutyl, cyclopentyl, cyclohexyl, cycloheptyl and cyclooctyl; benzyl; a phenyl group which may have a substituted group. Suitable substituents include an alkyl group having 1 to 5 carbon atoms, for example methyl, ethyl, propyl, isopropyl, n-butyl, pentyl, neopentyl, sec-butyl and tert-butyl; an alkoxy group having 1 to 5 carbon atoms, for example methoxy, ethoxy, propoxy, isopropoxy, n-butoxy, pentoxy, neopentoxy, sec-butoxy and tert-butoxy; acetyl group, chloroacetyl group, trichloroacetyl group, trifluoroacetyl group, carboxy group, amino group, a halogen atom such as fluorine, chlorine, bromine or iodine; nitrile group, sulfonyl group, nitro group and an ester group, for example methyl or ethyl ester. In this case, $R^1$ and $R^2$ may be identical or not, but for instance include methyl, ethyl, propyl, tert-butyl, benzyl and phenyl, and particular both includes phenyl. Diphenylphosphoryl azide (hereinafter it may be referred to as "DPPA".) is particularly preferred as the azide compound.

The azide compound may be added so as to effectively proceed with the reaction of halogenated trifluoroisophthalic acid. The amount of the azide compounds is usually in the range of 2 to 50 moles, and preferably in the range of 2 to 10 moles, per mole of halogenated trifluoroisophthalic acid, depending on the kinds or amounts of the halogenated trifluoroisophthalic acid, Lewis base, and solvent.

In Step 3c, it is essential to react halogenated trifluoroisophthalic acid with an azide compound in the presence of a Lewis base in a solvent. Suitable Lewis bases include an hydroxide of alkali metals such as sodium hydroxide, lithium hydroxide, potassium hydroxide, rubidium hydroxide and cesium hydroxide; an hydroxide of alkaline earth metals such as beryllium hydroxide, magnesium hydroxide, calcium hydroxide, strontium hydroxide and barium hydroxide; a primary amine such as methylamine, ethylamine, propylamine and n-, sec- and tert-butylamine, cyclohexylamine, benzylamine and phenylamine; a secondary amine such as dimethylamine, diethylamine, dipropylamine, dibutylamine, di-n-butylamine, di-sec-butylamine, di-tert-butylamine, dicyclohexylamine, dibenzylamine and diphenylamine; a tertiary amine such as trimethylamine, triethylamine, tripropylamine, tributylamine, tricyclohexylamine, tribenzylamine and triphenylamine; pyridine; a carbonate of alkali metals or alkaline earth metals such as sodium hydrogen carbonate, lithium hydrogen carbonate, potassium hydrogen carbonate, rubidium hydrogen carbonate, cesium hydrogen carbonate, sodium carbonate, lithium carbonate, potassium carbonate, rubidium carbonate, cesium carbonate, beryllium carbonate, magnesium carbonate, calcium carbonate, strontium carbonate and barium carbonate; a salt of alkali metals or alkaline earth metals such as potassium fluoride, potassium chloride, sodium fluoride, sodium chloride, calcium chloride and magnesium chloride, preferably triethylamine, trimethylamine, pyridine, sodium hydrogen carbonate, potassium hydrogen carbonate, potassium fluoride, sodium fluoride, and more preferably triethylamine, trimethylamine and pyridine.

The Lewis base is added to effectively proceed with the reaction of halogenated triisophthalonitrile, but for example usually in the range of 2 to 50 moles, and preferably in the range of 2 to 10 moles, per mole of halogenated trifluoroisophthalic acid. If the amount is less than 2 moles, halogenated trifluoroisophthalic acid does not effectively react, therefore it leads a drop of yields. In contrast, if the amount exceeds 50 moles, it does not obtain effects in proportion to additions, leads time-consuming, and finally increases in costs.

Suitable solvents include alcohols such as methanol, ethanol, dehydrated ethanol, isopropanol, benzylalcohol, phenol, and n-, sec- and tert-butanol; halogenated hydrocarbons such as chloroform, methylene chloride, carbon tetrachloride, chloroethane, and di-, tri- and tetra-chloroethane; hydrocarbons such as pentane, hexane, cyclohexane and heptane; aromatic hydrocarbons such as benzene, toluene and xylene; ethers such as diethylether, isopropylether, tetrahydrofuran (THF), dioxane, diphenylether, benzylether and tert-butylether, preferably alcohols in view of obtaining urethane which is easily hydrolyzed to amines, and most preferably tert-butanol, benzylalcohol and ethanol in view of obtaining amines easily under mild conditions such as catalytic reduction and acids in a cooled. The solvent may be added so as to effectively proceed with the reaction of halogenated trifluoroisophthalic acid, but for example in such a way that the concentration of halogenated trifluoroisophthalic acid in the solvent is usually in the range of 1 to 80 (w/v) %, and preferably in the range of 5 to 50 (w/v) %.

In Step 3c, halogenated trifluoroisophthalic acid and an azide compound are reacted to effectively proceed with the reaction, but the reaction temperature is usually in the range of −20° C. to 200° C., and preferably in the range of 20° C. to 150° C., and its duration is usually in the range of 0.1 to 40 hours, and preferably in the range of 0.1 to 20 hours. The reaction may be performed under a compressed, normal or a reduced pressure, but preferably under a normal pressure in view of easily handling and equipment.

The acid azide thus obtained is thermally rearranged and hydrolyzed, for example the acid azide is thermally rearranged in a first solvent at a temperature of −20° C. to 200° C., preferably in the range of 20° C. to 150° C. for 0.1 to 40 hours, preferably 0.1 to 20 hours, while refluxing if necessary, to form isocyanic ester in which the —$CON_3$ groups have been changed to —NCO groups. This isocyanic ester (10 weight parts) is hydrolyzed in a second solvent at a temperature of −50° C. to 200° C., preferably in the range of −20° C. to 150° C. for 0.1 to 40 hours, preferably 0.1 to 20 hours, while refluxing if necessary, using an acid or base in the range of 1 to 10000 weight parts, preferably in the range of 5 to 1000 weight parts. The objective HPC then can be produced.

Suitable first solvents include esters such as methyl formate, ethyl formate, methyl acetate, ethyl acetate and propyl acetate; ketones such as acetone, MIBK, cyclohexanone and methylethylketone; halogenated hydrocarbons such as chloroform, methylene chloride, carbon tetrachloride, chloroethane and di-, tri- and tetra-chloroethane; hydrocarbons such as pentane, hexane, cyclohexane and heptane; aromatic hydrocarbons such as benzene, toluene and xylene; ethers such as diethylether, isopropylether, THF, dioxane, diphenylether, benzylether and tert-butylether, and preferably chloroform, benzene and toluene.

Suitable second solvents include alcohols such as methanol, ethanol, dehydrated ethanol, isopropanol, benzylalcohol, phenol and n-, sec-, and tert-butanol; esters such as methyl formate, ethyl formate, methyl acetate, ethyl acetate and propyl acetate; ketons such as acetone, MIBK, cyclohexanone and MEK; halogenated hydrocarbons such as chloroform, methylene chloride, carbon tetrachloride, chloroethane and di-, tri-, and tetra-chloroethane; hydrocarbons such as pentane, hexane, cyclohexane and heptane; aromatic hydrocarbons such as benzene, toluene and xylene; ethers such as diethylether, isopropylether, THF, dioxane, diphenylether, benzylether and tert-butylether, and preferably methanol, ethanol, chloroform, benzene, toluene and ethyl acetate.

Suitable acids to be used in the hydrolysis include concentrated sulfuric acid, trichloroacetic acid, sulfuric acid, pyrophosphoric acid, triphosphoric acid, trimetaphosphoric acid, tetrametaphosphoric acid, trifluoroacetic acid, trifluoroacetic anhydride, hydrochloric acid, fuming sulfuric acid, concentrated hydrochloric acid, hydrobromic acid, propionic acid, formic acid, nitric acid and acetic acid; and mixtures thereof, for instance trifluoroacetic acid-trifluoroacetic anhydride (weight mixing ratio: 1:9 to 9:1, preferably 3:7 to 7:3) and trichloroacetic acid-sulfuric acid (weight mixing ratio: 1:9 to 9:1, preferably 3:7 to 7:3). The acid may be used singly or in a combination thereof. Among them, at least one selected from the group consisting of concentrated hydrochloric acid, hydrochloric acid, acetic acid, concentrated sulfuric acid, sulfuric acid, hydrobromic acid, and propionic acid; in particular concentrated hydrochloric acid, hydrochloric acid or sulfuric acid is preferably used as the acid. Suitable bases to be used in the hydrolysis include sodium hydroxide, lithium hydroxide, potassium hydroxide, rubidium hydroxide, cesium hydroxide, beryllium hydroxide, magnesium hydroxide, calcium hydroxide, strontium hydroxide and barium hydroxide, and preferably sodium hydroxide, potassium hydroxide, lithium hydroxide and calcium hydroxide. The base may be used singly or in a combination thereof.

In the hydrolysis above, if hydrolysate is present in the form of a hydrochloric acid salt, this hydrolysate may be neutralized with a base. Suitable bases to be used are the same as the above hydrolysis. The acid azide may be used as it is, which is produced from the reaction of halogenated trifluoroisophthalic acid and the azide compound. The concentration of the acid azide in the first solvent is usually in the range of 1 to 80 (w/v) %, and preferably in the range of 5 to 50 (w/v) %. The isocyanic ester obtained from thermal rearrangement of the acid azide may be used as it is. The concentration of the isocyanic ester in the second solvent is usually in the range of 1 to 80 (w/v) %, and preferably in the range of 5 to 50 (w/v)%. Thermal rearrangement and hydrolysis may be performed under a compressed, normal or a reduced pressure, and preferably under normal pressure in view of easy handling and equipment.

The halogenated trifluoroisophthalic acid obtained in Step 3b is reacted with an azide compound in the presence of a Lewis base in a solvent to produce an acid azide in which the carboxyl groups in the halogenated trifluoroisophthalic acid are changed to —$CON_3$ groups. This acid azide is reacted with an alcohol in a steam bath at a temperature of −20° C. to 200° C., preferably 20° C. to 150° C., for 0.1 to 40 hours, preferably 0.1 to 20 hours, while refluxing if necessary, to form a urethane. Further, this urethane is hydrolyzed in a third solvent with an acid or base usually in the range of 1 to 10000 weight parts, preferably in the range of 5 to 1000 weight parts, based on 10 weight parts of the urethane usually at a temperature of −50° C. to 200° C., preferably of −20° C. to 150° C., for 0.1 to 40 hours, preferably 0.1 to 20 hours, while refluxing if necessary. The objective halogenated m-phenylenediamine then may be produced, instead of Step 3c.

Suitable alcohols to be used in the reaction of the acid azide include methanol, ethanol, dehydrated ethanol, isopropanol, benzylalcohol, phenol, and n-, sec- and tert-butanol or the like.

The reaction of the acid azide and alcohol may be performed without addition of solvents, since the alcohol is a liquid. However, other solvents may be added depending on the kinds and amounts of the raw materials and reaction conditions. Suitable solvents in this case include water, esters such as methyl formate, ethyl formate, methyl acetate, ethyl acetate and propyl acetate; ketones such as acetone, MIBK, cyclohexanone and MEK; halogenated hydrocarbons such as chloroform, methylene chloride, carbon tetrachloride, chloroethane and di-, tri-, and tetra-chloroethane; hydrocarbons such as pentane, hexane, cyclohexane and heptane; aromatic hydrocarbons such as benzene, toluene and xylene; ethers such as diethylether, isopropylether, THF, dioxane, diphenylether, benzylether and tert-butylether.

Suitable third solvents to be used in the above hydrolysis include water; alcohols such as methanol, ethanol, dehydrated ethanol, isopropanol, benzylalcohol, phenol and n-, sec-, and tert-butanol; esters such as methyl formate, ethyl formate, methyl acetate, ethyl acetate and propyl acetate; ketons such as acetone, MIBK, cyclohexanone and MEK; halogenated hydrocarbons such as chloroform, methylene chloride, carbon tetrachloride, carbon tetrachloride, chloroethane and di-, tri-, and tetra-chloroethane; hydrocarbons such as pentane, hexane, cyclohexane and heptane; aromatic hydrocarbons such as benzene, toluene and xylene; ethers such as diethylether, isopropylether, THF, dioxane, diphenylether, benzylether and tert-butylether, and preferably methanol, ethanol, chloroform, benzene, toluene and ethyl acetate.

Suitable acids to be used in the hydrolysis include concentrated sulfuric acid, trichloroacetic acid, sulfuric acid, pyrophosphoric acid, triphosphoric acid, trimetaphosphoric acid, tetrametaphosphoric acid, trifluoroacetic acid, trifluoroacetic anhydride, hydrochloric acid, fuming sulfuric acid, concentrated hydrochloric acid, hydrobromic acid, propionic acid, formic acid, nitric acid and acetic acid; and mixtures thereof, for instance trifluoroacetic acid-trifluoroacetic anhydride (weight mixing ratio: 1:9 to 9:1, preferably 3:7 to 7:3) and trichloroacetic acid-sulfuric acid (weight mixing ratio: 1:9 to 9:1, preferably 3:7 to 7:3). The acid may be used singly or in a combination thereof. Among them, at least one selected from the group consisting of concentrated hydrochloric acid, hydrochloric acid, acetic acid, concentrated sulfuric acid, sulfuric acid, hydrobromic acid, and propionic acid; in particular concentrated hydrochloric acid, hydrochloric acid or sulfuric acid is preferably used as the acid. Suitable bases to be used in the hydrolysis include sodium hydroxide, lithium hydroxide, potassium hydroxide, rubidium hydroxide, cesium hydroxide, beryllium hydroxide, magnesium hydroxide, calcium hydroxide, strontium hydroxide and barium hydroxide, and preferably sodium hydroxide, potassium hydroxide, lithium hydroxide and calcium hydroxide. The base may be used singly or in a combination thereof.

In the hydrolysis above, if hydrolysate is present in the form of a hydrochloric acid salt, this hydrolysate may be neutralized with a base. Suitable bases to be used are the same as the above hydrolysis. The acid azide may be used as it is, as described above. The concentration of the acid azide in the alcohol and other solvent added is usually in the range of 1 to 80 (w/v) %, and preferably in the range of 5 to 50 (w/v) %. The urethane obtained from thermal rearrangement of the acid azide may be used as it is. The concentration of the urethane in the third solvent is usually in the range of 1 to 80 (w/v) %, and preferably in the range of 5 to 50 (w/v) %. Thermal rearrangement and hydrolysis may be performed under a compressed, normal or a reduced pressure, and preferably under normal pressure in view of easy handling and equipment.

The TPC thus obtained can be purified by conventional purifications, for example column chromatographs with silica gel or alumina, distillation preferably solid distillation, re-crystallization, re-precipitation and sublimation.

The tetrafluoro-m-phenylenediamine including HPC are important intermediates for synthesizing dye, medicine, agricultural chemical and macromolecule compounds, and useful for raw materials of resins excellent in heat resistance, water repellent property, chemical resistance, and low dielectric property. Furthermore, these are suitably used for charge-transfer agents (in particular positive hole-transfer agents) in the fields of solar battery, electroluminescent elements, and electrophotography photosensitive body.

The HPC has a relatively high melting point, and low solubility into dimethylacetoamide, thus excels in heat resistance and chemical resistance.

In accordance with the present invention, it can provide new HPC. The HPCs are important intermediates for synthesizing dye, medicine, agricultural chemical and macromolecule compounds, and expected to be useful for raw materials of resins excellent in heat resistance, water repellent property, chemical resistance, and low dielectric property.

(Fluorine Compound)

The present invention relates to a fluorine compound represented by the formula 41:

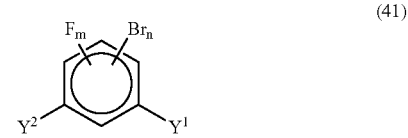

(41)

In Formula 41, n indicates the bonding number of bromine atom to the benzene ring, an integer of 1 to 3, preferably 1 or 2, and more preferably 1. The bonding place of the bromine atom to the benzene ring depends on the bonding number of the bromine atom and the property of the objective fluorine compound. For example, one bromine atom bonds to the position 4 or 5 of the benzene ring if n is 1, and two bromine atoms bond to the positions 4 and 6 thereof if n is 2.

In formula 41, $Y^1$ and $Y^2$ indicate carboxyl (—COOH) or cyano (—CN) groups, wherein $Y^1$ and $Y^2$ may be same or not, but preferably same. The term m indicates the bonding number of fluorine atom to the benzene ring, an integer of 3 to 1, preferably 3 or 2, and more preferably 3. In the formula 41, the sum of n and m is 4, so that the compound represented by the formula 41 does not have any carbon-hydrogen bonds.

Suitable fluorine compounds of the present invention include 4-bromo-2,5,6-trifluoroisophthalonitrile, 5-bromo-2,4,6-trifluoroisophthalonitrile, 4,6-dibromo-2,5-difluoroisophthalonitrile, 4-bromo-2,5,6-trifluoroisophthalonitrile, 5-bromo-2,4,6-trifluoroisophthalonitrile, and 4,6-dibromo-2,5-difluoroisophthalonitrile.

In the above compounds, trifluoroisophthalonitrile compounds and trifluoroisophthalic acids are referred to as halogenated trifluoroisophthalonitrile and halogenated trifluoroisophthalic acid, respectively.

Among them, 4-bromo-2,5,6-trifluoroisophthalonitrile and 4-bromo-2,5,6-trifluoroisophthalic acid are preferable.

The fluorine compound of the present invention may be produced by conventional methods. The present method can be divided into two: halogenated trifluoroisophthalonitrile and halogenated trifluorophthalic acid.

The methods of halogenated trifluoroisophthalonitrile of the present invention will be explained. The halogenated trifluoroisophthalonitrile will be produced by the conventional methods, for example the method described in JP-B-63-5023.

A first embodiment for producing a halogenated trifluoroisophthalonitrile of the present invention will be explained below. Tetrafluoroisophthalonitrile is reacted with a brominating agent to replace the fluorine atom bonded to the benzene ring with the bromine atom. For example, by specifically substituting the fluorine at the 4-position in tetrafluoroisophthalonitrile, 4-bromo-2,5,6-trifluoroisophthalonitrile can be obtained in a high yield.

Suitable brominating agents include known brominating agents, but for example sodium bromide, potassium bromide and lithium bromide. Sodium bromide and potassium bromide are preferable in view of readily handling and availability.

The brominating agent may be added to specifically substitute the fluorine atom at the 4-position in tetrafluoroisophthalonitrile with a bromine atom or more, but for example in the range of 1 to 5 moles, and preferably in the range of 1 to 2 moles, per mol of tetrafluoroisophthalonitrile. If it exceeds 5 moles, there is a fear that fluorine atoms except for the 4-position in tetrafluoroisophthalonitrile will be substituted with a bromine atom, and further it is necessary to treat the remaining brominating agent, and therefore not economically. In contrast, if it is less than 1 mole, the fluorine atom in the 4-position will not be fully substituted with such an agent, and unreacted raw material will remain in a large amount.

The bromination of tetrafluoroisophthalonitrile may be performed in the presence or absence of a solvent, but preferably in the presence of the solvent. Suitable solvents include those which do not block such a bromination, and are inert for the brominating agent, but for example nitrites such as acetonitrile and benzonitrile; ketones such as acetone, methylisobutylketone (MIBK), methylethylketone (MEK) and cyclohexanone; halogenated hydrocarbons such as chloroform, methylene chloride, carbon tetrachloride, chloroethane and di-, tri-, tetra-chloroethane; aromatic hydrocarbons such as benzene, toluene and xylene; hydrocarbons such as pentane, hexane, cyclohexane and heptane; ethers such as diethylether, isopropylether, tetrahydrofuran (THF), dioxane, diphenylether, benzylether and tert-butylether; esters such as methyl formate, ethyl formate, methyl acetate, ethyl acetate, propyl acetate and isopropyl acetate; N-methylpyrrolidinone (NMP), dimethylformamide (DMF), dimethylsulfoxide (DMSO), dimethylacetamide, sulfolan ($TMSO_2$) and dimethylsulfolan ($DMSO_2$); and more preferably acetonitrile, benzonitrile, NMP, DMF and DMSO. The solvent may be used in such a way that the concentration of tetrafluoroisophthalonitrile in the solvent is usually in the range of 2 to 80 (w/v) %, and more preferably in the range of 5 to 50 (w/v) %. The bromination reaction may be performed preferably free from water so as to improve reaction velocity and prevent side reactions. In using solvents having a high hygroscopic property such as dimethylsulfoxide, sulfolan, dimethylformamide, N-methylpyrrolidinone and dimethylsulforan, benzene or toluene is added therein preferably so as to remove the water therefrom prior to the substitution reaction.

Tetrafluoroisophthalonitrile and the brominating agent are reacted to fully proceed with the halogen substitution reaction, but the reaction temperature is usually in the range of 0° C. to 300° C., and preferably in the range of 50° C. to 250° C., and the reaction duration is usually in the range of 0.5 to 20 hours. The reaction may be performed under a reduced, normal or a compressed pressure, and preferably at normal pressure.

In a second embodiment, a halogenated trifluoroisophthalonitrile may be produced by fluorinating tetrabromoisophthalonitrile with a fluorinating agent. The bromine atoms in the 2, 4, and 6 positions in tetrabromoisophthalonitrile are specifically substituted with the fluorine atoms by means of nucleophilic substitution reaction to form a desired 5-bromo-2,4,6-trifluoroisophthalonitrile in a high yield.

Suitable fluorinating agents include known fluorinating agents, but for example potassium fluoride, cesium fluoride, sodium fluoride, barium fluoride, calcium fluoride and antimony fluoride, and preferably potassium fluoride in view of handling property and acquisition with ease.

The fluorinating agent may be added to specifically fluorinate the bromine atoms in the 2,4,6 positions in tetrabromoisophthalonitrile, but stoichiometrically three times per mole of the raw material. Concretely, the fluorinating agent is usually in the range of 3 to 20 moles, and preferably 3 to 10 moles, per mole of tetrabromoisophthalonitrile. If it exceeds 20 moles, there is a fear that the 5-position will be additionally fluorinated, and further it is necessary to treat the remaining fluorinating agents, so that not economical. In contrast, if it is less than 3 moles, the bromine atoms in the 2, 4, 6 positions are not fully fluorinated, thereby the yield of the objective product will be lowered.

The fluorinating reaction for tetrabromoisophthalonitrile may be performed in the presence or absence of a solvent, but preferably in the presence of the solvent. Suitable solvents include those which do not block the fluorinating reaction and are inert for tetrabromoisophthalonitrile and the fluorinating agents, but for example benzonitrile, DMSO, sulfolan ($TMSO_2$), DMF, N-methylpyrrolidinone (NMP), dimethylsulfolan ($DMSO_2$), acetonitrile, acetone, MEK and MIBK, and preferably benzonitrile and acetonitrile. The solvent may be used in such a way that the concentration of tetrabromoisophthalonitrile is usually in the range of 1 to 80 (w/v) %, and preferably 5 to 50 (w/v) %. The fluorination is preferably performed free from water so as to increase reaction velocity and prevent side reactions. For this purpose, in using solvents having a high hygroscopic property such as dimethylsulfoxide, sulfolan, dimethylformamide, N-methylpyrrolidinone and dimethylsulforan, benzene or toluene is added therein preferably so as to remove the water therefrom prior to the substitution reaction.

Tetrabromoisophthalonitrile and the fluorinating agent are reacted to fully proceed with the fluorination. The reaction temperature is usually in the range of 50° C. to 400° C., and preferably in the range of 100° C. to 300° C. The reaction duration is usually 0.5 to 20 hours. The reaction may be performed under a reduced, normal or a compressed pressure, but preferably either normal or a compressed pressure. In the case of a compressed pressure, it is preferably in the range of 30 to 1000 kPa, and more preferably in the range of 100 to 800 kPa.

The fluorination may be performed in the presence of a phase-transfer catalyst so as to heighten the fluorination reaction velocity. Suitable phase-transfer catalysts include known phase-transfer catalysts, but for example crown compounds such as dibenzo-18-crown-6-ether and polyethylene glycol (molecular weight: 300 to 600). The catalyst may be added in the range of 0.1 to 10 moles, per mole of tetrabromoisophthalonitrile.

The halogenated trifluoroisophthalonitrile thus obtained can be purified by conventional purifications, for example column chromatographs with silica gel or alumina, distillation preferably solid distillation, re-crystallization, re-precipitation and sublimation.

The method of halogenated trifluoroisophthalic acid of the present invention will be explained.

The halogenated trifluoroisophthalic acid of the present invention can be produced by conventional methods, for example the halogenated trifluoroisophthalonitrile thus obtained is hydrolyzed to change the cyano groups to carboxyl groups. Alternatively, the halogenated trifluoroisophthalic acid can be also produced by halogenating compounds in which m-xylene, m-dialkyl benzene and the hydrogen atoms of these alkyl groups substituted with other atoms or an atomic group, and then oxidizing the alkyl groups. Among them, the hydrolysis method is preferably cited, so that it will be explained below.

The hydrolysis of halogenated trifluoroisophthalonitrile is performed in the presence of an acid or base. Suitable acids include concentrated sulfuric acid, trichloroacetic acid, sulfuric acid, pyrophosphoric acid, triphosphoric acid and tri- and tetra-metaphosphoric acid; trifluoroacetic acid, trifluoroacetic anhydride, hydrochloric acid, fuming sulfuric acid, concentrated hydrochloric acid, hydrobromic acid, propionic acid, formic acid, nitric acid, acetic acid; mixtures thereof for instance trifluoro acetic acid-trifluoroacetic anhydride (mixing ratio by weight: 1:9 to 9:1, preferably 3:7 to 7:3) and trichloroacetic acid-sulfuric acid (mixing ratio by weight: 1:9 to 9:1, preferably 3:7 to 7:3). The above acid may be used singly or in a combination thereof, and as it is or in the form of an aqueous solution. In the case of the solution, the acid can be used to fully hydrolyze halogenated trifluoroisophthalonitrile or more, but for example in the range of 40 to 85% by weight, depending on the reaction temperature and kinds of the acid. Among them, sulfuric acid, in particular an aqueous 50 to 80% by weight of sulfuric acid is preferably used. Among them, at least one selected from the group consisting of polyphosphoric acid, trifluoroacetic acid-trifluoroacetic anhydride, trichloroacetic acid, propionic acid, hydrochloric acid, concentrated hydrochloric acid and sulfuric acid, in particular sulfuric acid, propionic acid, concentrated hydrochloric acid and polyphosphoric acid are preferably used. Suitable bases include sodium hydroxide, lithium hydroxide, potassium hydroxide rubidium hydroxide, cesium hydroxide, beryllium hydroxide, magnesium hydroxide, calcium hydroxide, strontium hydroxide and barium hydroxide, and preferably sodium hydroxide, potassium hydroxide, calcium hydroxide and barium hydroxide. Also, the above base may be used singly or in a combination thereof. The acid or base is added to fully hydrolyze halogenated trifluoroisophthalonitrile, but for example the concentration of halogenated trifluoroisophthalonitrile to the acid or base to be added may be in the range of 1 to 80% by weight, and preferably in the range of 5 to 50% by weight.

Halogenated trifluoroisophthalonitriles should be fully hydrolyzed, but for instance the hydrolysis temperature is usually in the range of −20° C. to 200° C., preferably in the range of 0° C. to 150° C., and its duration is usually in the range of 0.1 to 40 hours, and preferably in the range of 0.1 to 20 hours. The hydrolysis may be performed under a compressed, normal or a reduced pressure, and preferably under a normal pressure.

The halogenated trifluoroisophthalic acid thus obtained is purified by conventional purifications, for example column chromatographs with silica gel or alumina, distillation preferably solid distillation, re-crystallization, re-precipitation and sublimation.

The tetrafluoro-m-phenylenediamine including HPC are important intermediates for synthesizing dye, medicine, agricultural chemical and macromolecule compounds, and useful for raw materials of resins excellent in heat resistance, water repellent property, chemical resistance, and low dielectric property. Furthermore, these are suitably used for charge-transfer agents (in particular positive hole-transfer agents) in the fields of solar battery, electroluminescent elements, and electrophotography photosensitive body.

In accordance with the present invention, it can provide new fluorine compounds. The fluorine compounds are important intermediates for synthesizing dye, medicine, agricultural chemical and macromolecule compounds, and expected to be useful for raw materials of resins excellent in heat resistance, water repellent property, chemical resistance, and low dielectric property.

EXAMPLE

Now, the present invention will be explained referring to examples, but not restricted by these examples.

(HAA)

Synthesis Example 1

In a 500 ml 4-necked flask, were poured 71.15 g (355 mmol) of tetrafluorophthalonitrile, 2.16 g (37.1 mmol) of potassium fluoride and 210 g of acetonitrile, and resulting was heated to 80° C. This mixture was kept at 80° C. with stirring, and to this mixture were dropped 4.40 g (17.7 mmol) of tetrachlorohydroquinone in 200 ml of acetonitrile over 1 hour. After dropping, reaction was performed at 80° C. for 6 hours. The reaction solution was cooled, filtrated, and the resulting residue washed with 30 ml and 15 ml of acetonitrile. After the filtrate had been concentrated on an evaporator to remove the solvent, 62.34 g of tetrafluorophthalonitrile was removed under in vacuo. To this was poured 27 ml of toluene and reflux performed for 1 hour. After cooling, the residue was washed with 5 ml, 25 ml and 5 ml of toluene, respectively, and further 12 ml of deionized water for three times. Finally, by drying the residue at 70° C. in vacuo, 9.08 g of 1,4-bis(3,4-dicyanotrifluorophenoxy)tetrachlorobenzene were obtained (yield: 84%).

Synthesis Example 2

In a 100 ml 3-necked flask, were poured 69.2 g of a 70% sulfuric acid and 4.2 g of 1,4-bis(3,4-dicyanotrifluorophenoxy)tetrachlorobenzene synthesized in Synthesis Example 1. The inner temperature was heated to 130° C., and continued for 6 hours at this temperature. Then, to the reaction solution were added 175 g of ice water to precipitate. After filtration, the residue was washed with 30 ml of water for 2 times. Then, this residue was re-crystallized in 400 ml of an aqueous 10 wt. % acetone solution.

After repeating the procedure as the above for 4 times, vacuum drying at 100° C. for 16 hours were performed to give 8.63 g of 1,4-bis(3,4-dicarboxytrifluorophenoxy)tetrachlorobenzene (yield: 71%).

Example 1

In a 100 ml 3-necked flask, were added 3.45 g (5.04 mmol) of 1,4-bis(3,4-dicarboxytrifluorophenoxy)tetrachlorobenzene synthesized in Synthesis Example 2 and 53.5 g (640.72 mmol) of thionyl chloride, and the inner temperature was heated to 70° C. After reaction at this temperature for 3 hours, the reaction solution was cooled. Then, 9.4 g of thionyl chloride were removed from the solution with a Dean-Stark tube, and then 8 ml of acetone were added and mixed. After filtration, the crystal was washed in 10 ml of toluene with stirring. After filtration, the residue was washed with toluene. The resulting crystal was dried in vacuo (100° C. for 20 hours) to offer 8.4 g of 1,4-bis(3,4-dicarboxytrifluorophenoxy)tetrachlorobenzene dianhydride (yield: 72.9%).

This product was measured by a mass spectrum analysis to be found $M^+=646$. When the product was analyzed by a $^{19}$F-NMR spectrometer, the spectrum depicted in FIG. 1 was obtained. Melting Point (ThermoGravimetry-Differential Thermal Analysis available from Seiko Instruments in Japan): 305° C. The solubility to dimethylacetoamide at 25° C. was 22 wt. %. This solution was left standing for a night, but precipitations were not found.

(HTC)

Example II-1

1,4-bis(3,4-dicyanotrifluorophenoxy)tetrachlorobenzene

In a 500 ml 4-necked flask, were placed 71.15 g (355 mmol) of tatrafluorophthalonitrile, 2.16 g (37.1 mmol) of potassium fluoride and 210 g of acetonitrile, and the inner temperature was heated to 80° C. While this mixture was stirred at 80° C., 4.40 g (17.7 mmol) of tetrachlorohydroquinone in 200 ml of acetonitrile were dropped over 1 hour. After dropping, reaction was performed at 80° C. for 6 hours, the reaction solution cooled. After filtration, the residue was washed with 30 ml and 15 ml of acetonitrile, respectively. After the filtrate had been concentrated on an evaporator to remove the solvent, 62.34 g of tetrafluorophthalonitrile was removed under in vacuo. To this was poured 27 ml of toluene and reflux performed for 1 hour. After cooling, the residue was washed with 5 ml, 25 ml and 5 ml of toluene, respectively, and further 12 ml of deionized water for three times. Finally, by drying the residue at 70° C. in vacuo, 9.08 g of 1,4-bis(3,4-dicyanotrifluorophenoxy)tetrachlorobenzene were obtained (yield: 84% based on tetrachlorohydroquinone).

Figure 2:
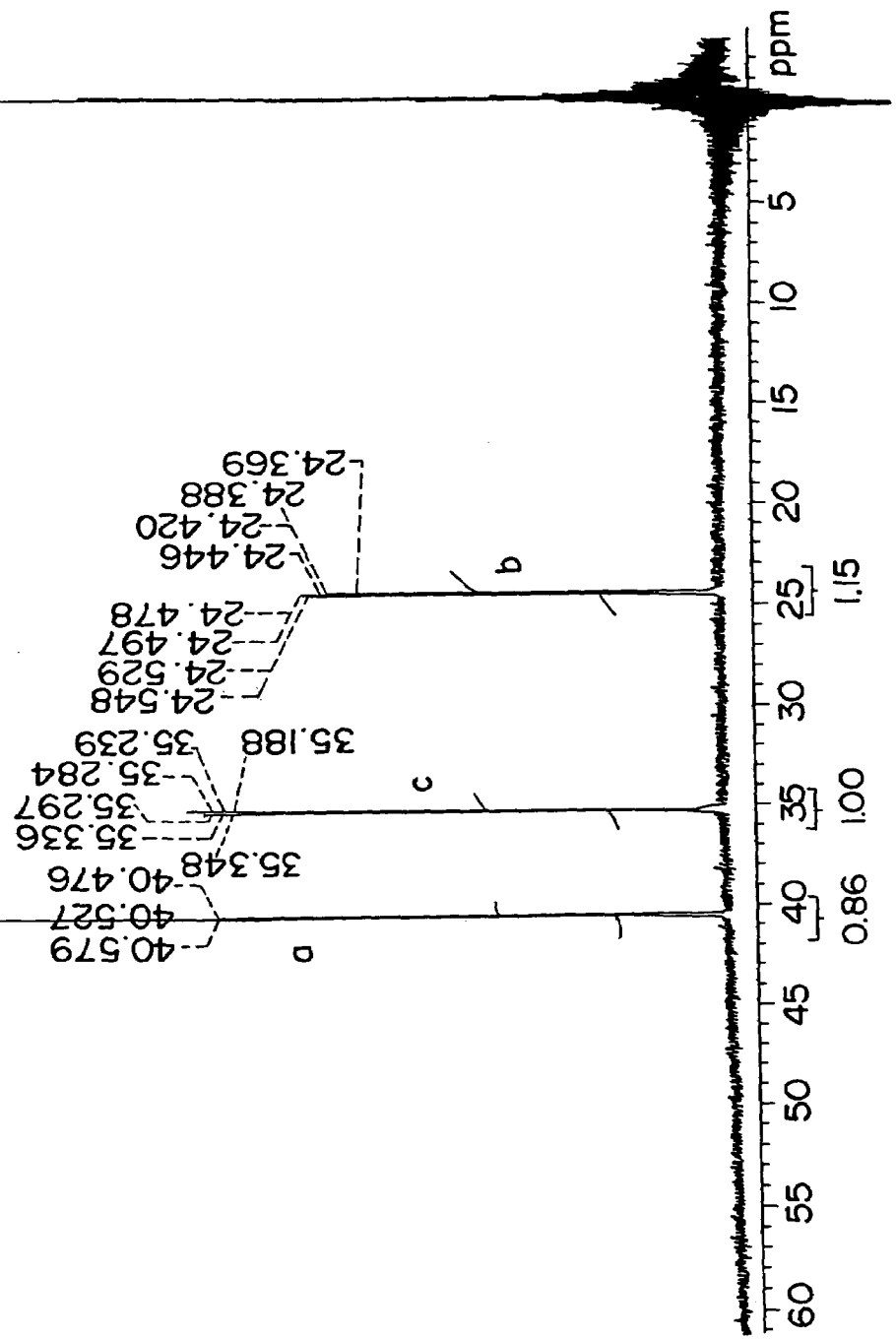
FIG. 2 shows a graph of $^{19}$F-NMR spectrum for 1,4-bis (3,4-dicyanotrifluorophenoxy)tetrachlorobenzene obtained in Example II-1.

This product was measured by a mass spectrum analysis to be found $M^+=606$. When the product was analyzed by a $^{19}$F-NMR spectrometer, the spectrum depicted in FIG. 2 was obtained.

Example II-2

1,4-bis(3,4-dicarboxytrifluorophenoxy)tetrachlorobenzene

In a 100 ml 3-necked flask, were poured 69.2 g of a 70% sulfuric acid and 4.2 g of 1,4-bis(3,4-dicyanotrifluorophenoxy)tetrachlorobenzene synthesized in Example II-1. The inner temperature was heated to 130° C., and continued for 6 hours at this temperature. Then, to the reaction solution were added 175 g of ice water to precipitate. After filtration, the residue was washed with 30 ml of water for 2 times. Then, this residue was re-crystallized in 400 ml of an aqueous 10 wt. % acetone solution.

After repeating the procedure as the above for 4 times, vacuum drying at 100° C. for 16 hours was performed to give 8.63 g of 1,4-bis(3,4-dicarboxytrifluorophenoxy)tetrachlorobenzene (yield: 71% based on 1,4-bis(3,4-dicyanotrifluorophenoxy)tetrachlorobenzene).

Figure 3:
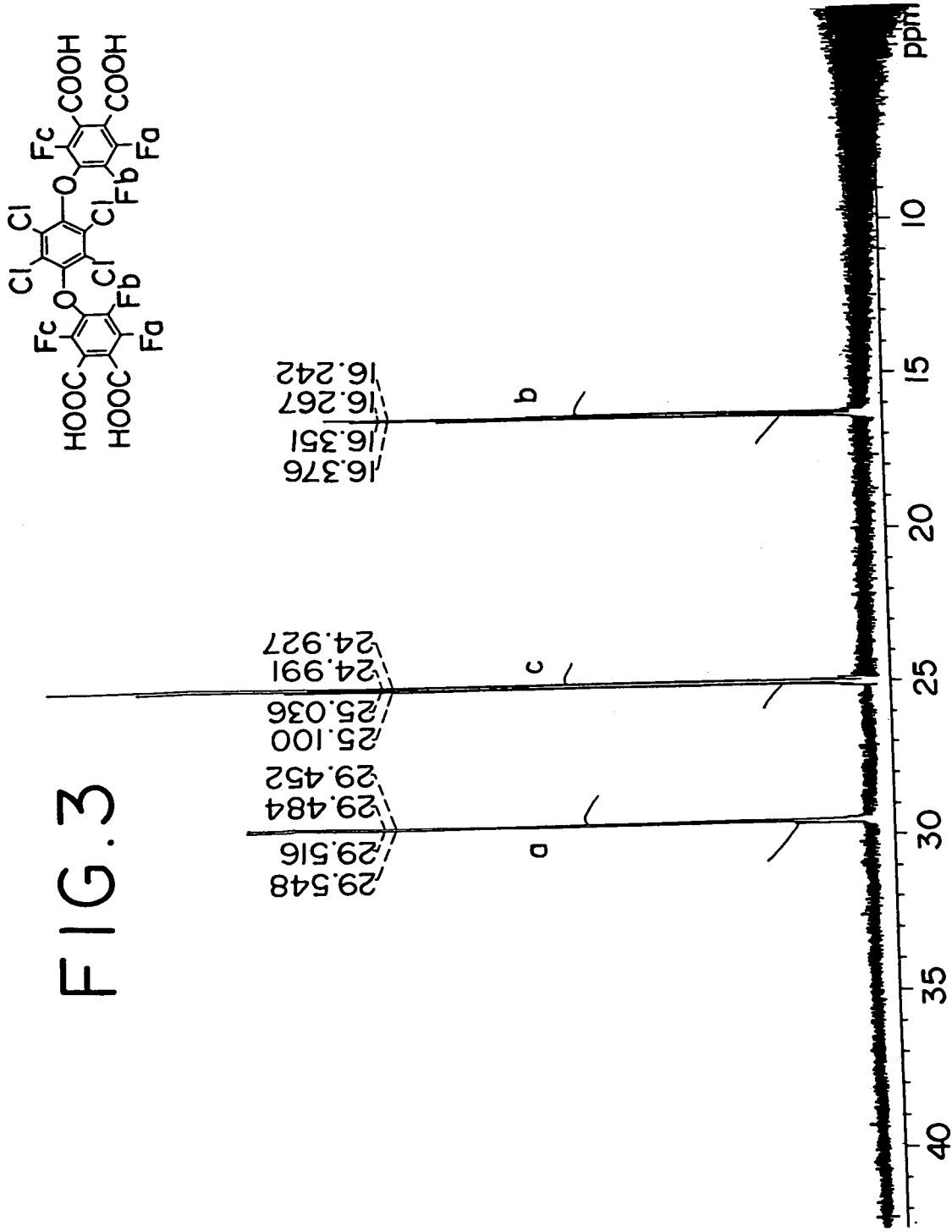
FIG. 3 shows a graph of $^{19}$F-NMR spectrum for 1,4-bis (3,4-dicarboxytrifluorophenoxy)tetrachlorobenzene obtained in Example II-2.

This product was measured by a mass spectrum analysis to be found $M^+=682$. When the product was analyzed by a $^{19}$F-NMR spectrometer, the spectrum depicted in FIG. 3 was obtained.

Example II-3

In a 1000 ml 4-necked flask, were placed 50 g of 1,4-bis(3,4-dicyanotrifluorophenoxy)tetrachlorobenzene synthesized in Example II-1 and 350 ml of propionic acid. While stirring this mixture at 130° C., 150 ml of a 70 wt. % sulfuric acid were dropped over 1 hour, and then refluxed for 6 hours. After cooling, the refluxed solution was poured into 1.5 liter of ice water. After filtration, the residue was washed with 100 ml of water, and then re-crystallized in 500 ml of an aqueous 10 wt. % acetone solution. The re-crystallization procedure was repeated once. The resulting crystal was dried at 100° C. for 5 hours to give 43.9 g of 1,4-bis(3,4-dicarboxytrifluorophenoxy)tetrachlorobenzene (yield: 78% based on 1,4-bis(3,4-dicyanotrifluorophenoxy)tetrachlorobenzene).

Example II-4

In a 3000 ml 4-necked flask, were placed 0.50 g of 1,4-bis(3,4-dicyanotrifluorophenoxy)tetrachlorobenzene synthesized in Example II-1 and 700 ml of acetic acid. While stirring this mixture at 100° C., 300 ml of a 70 wt. % sulfuric acid were dropped over 1 hour, and then refluxed for 14 hours. After cooling, the refluxed solution was poured into 1.5 liter of ice water. After filtration, the residue was washed with 100 ml of water, and then re-crystallized in 400 ml of an aqueous 10 wt. % acetone solution twice. The resulting crystal was dried at 100° C. for 5 hours to give 38.2 g of 1,4-bis(3,4-dicarboxytrifluorophenoxy)tetrachlorobenzene (yield: 68% based on 1,4-bis(3,4-dicyanotrifluorophenoxy)tetrachlorobenzene).

Example II-5

1,4-bis(3,4-dicarboxytrifluorophenoxy)tetrachlorobenzene dianhydride

In a 100 ml 3-necked flask, were added 3.45 g (5.04 mmol) of 1,4-bis(3,4-dicarboxytrifluorophenoxy)tetrachlorobenzene synthesized in Example II-2 and 53.5 g (640.72 mmol) of thionyl chloride, and the inner temperature was heated to 70° C. After reaction at this temperature for 3 hours, the reaction solution was cooled. Then, 9.4 g of thionyl chloride were removed from the solution with a Dean-Stark tube, and then 8 ml of acetone were added and mixed. After filtration, the crystal was washed in 10 ml of toluene with stirring. After filtration, the residue was washed with 15 ml of toluene. The resulting crystal was dried in vacuo (100° C. for 20 hours) to offer 8.4 g of 1,4-bis(3,4-dicarboxytrifluorophenoxy)tetrachlorobenzene dianhydride (yield: 72.9%: based on 1,4-bis(3,4-dicarboxytrifluorophenoxy)tetrachlorobenzene).

(HPC)

Synthesis Example III-1

In a 3 liter reaction vessel, were added 200 g (1.00 mol) of tetrafluoroisophthalonitrile, 1 liter of N-dimethylformamide (DMF) and 102.7 g (1.00 mol) of sodium bromide (NaBr). This mixture was heated at 120° C. for 1 hour. Separately, 3 liter of water was poured to a 5 liter of beaker, and to which was poured the resulting reaction solution. After suction filtration, the residue was washed with water and hexane, and then dried in vacuo to offer 198.2 g of a white solid. The solid was purified by means of solid distillation to give 142.8 g (0.55 mol) of 4-bromo-2,5,6-trifluoroisophthalonitrile as a white solid (yield: 55%).

Figure 4:
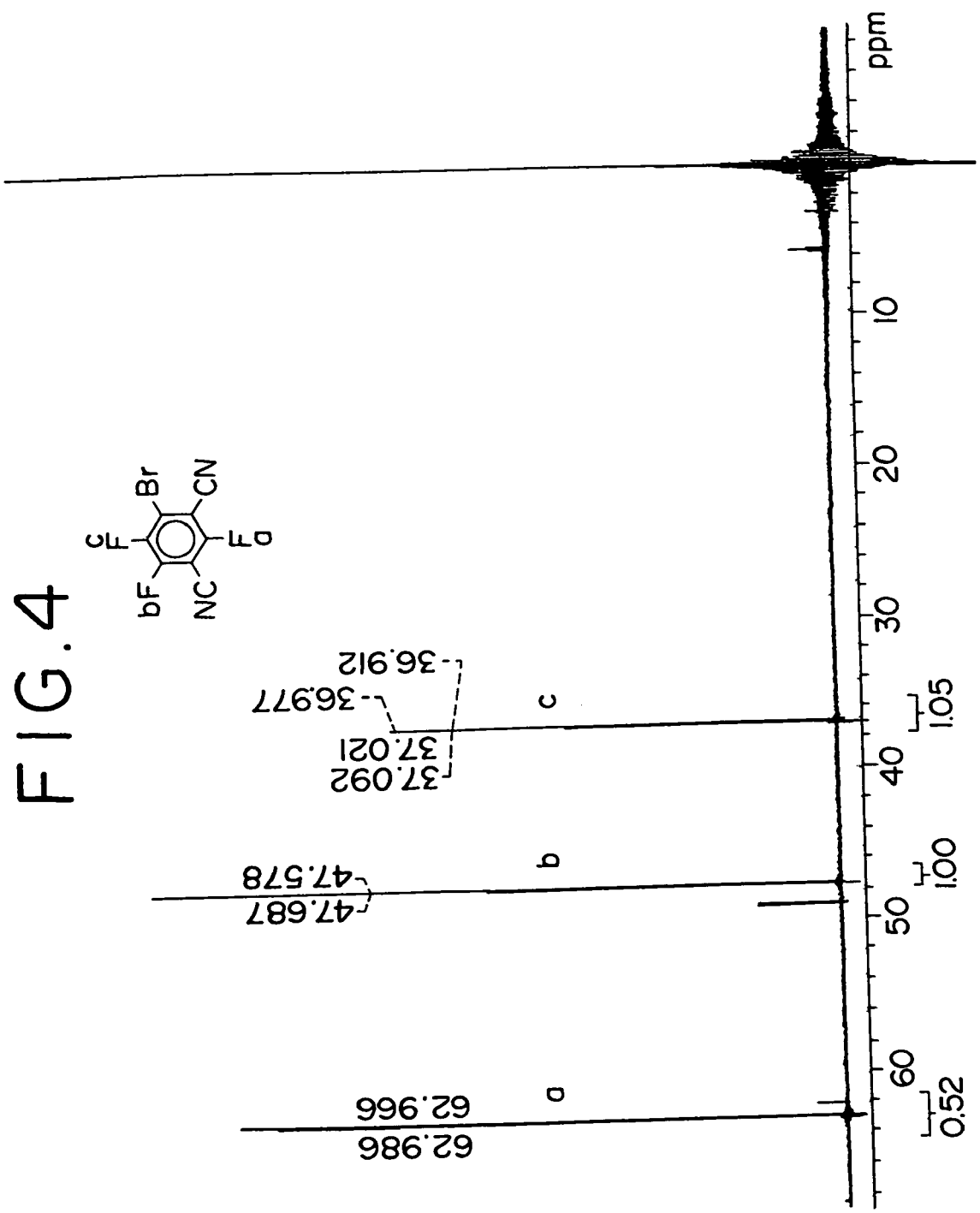
FIG. 4 shows a graph of $^{19}$F-NMR spectrum for 4-bromo-2,5,6-trifluoroisophthalonitrile obtained in Synthesis Example III-1.

This product was measured by a mass spectrum analysis to be found M$^+$=260. When the product was analyzed by a $^{19}$F-NMR spectrometer, the spectrum depicted in FIG. 4 was obtained.

Synthesis Example III-2

In a 500 ml autoclave made of stainless steel, were placed 200.0 g of benzonitrile, 80.0 g (0.301 mol) of tetrachloroisophthalonitrile and 83.9 g (1.445 mol) of finely divided, dried potassium fluoride, and the air therein was replaced with nitrogen gas. This mixture was heated at 220° C. for 18 hours with stirring. The reactant was cooled to room temperature, and suspended potassium chloride and unreacted potassium fluoride were removed by means of filtration. By removing benzonitrile from the filtrate by vacuum distillation, 42.8 g (0.198 mole) of 5-chloro-2,4,6-trifluoroisophthalonitrile were obtained as a white solid (yield: 65.8%).

Synthesis Example III-3

In a 5 liter reaction vessel, 250 g (1.15 mol) of 5-chloro-2,4,6-trifluoroisophthalonitrile and 2500 ml of an aqueous 62% sulfuric acid solution, and then reflux was performed for 3 hours. This solution was cooled to 25° C. After filtration, the crystal was dissolved in 500 ml of isopropyl ether (IPE), and then washed with 500 ml of a saturated aqueous NaCl solution. Then, this crystal was dried with magnesium sulfate, and by removing the solvent (IPE) by an evaporator, 280.3 g (1.10 mol) of 5-chloro-2,4,6-trifluoroisophthalic acid were obtained as a white solid (yield: 95.4%).

Synthesis Example III-4

In a 200 ml 4-necked flask, were added 20.03 g (76.74 mmol) of 4-bromo-2,5,6-trifluoroisophthalonitrile, 40 ml of an aqueous 62% sulfuric acid solution and 40 ml of propionic acid, and reflux was performed at 130° C. for 18 hours. This solution was cooled to room temperature. After suction filtration, the residue was washed with a small amount of water. Then, this crystal was dissolved into 200 ml of IPE, and washed with 100 ml of water and 100 ml of a saturated aqueous NaCl solution. Further, this crystal was dried with magnesium sulfate, and the IPE removed on an evaporator to give 17.2 g (57.53 mmol) of a white solid of 4-bromo-2,5,6-trifluoroisophthalic acid (yield: 75.0%).

Figure 5:
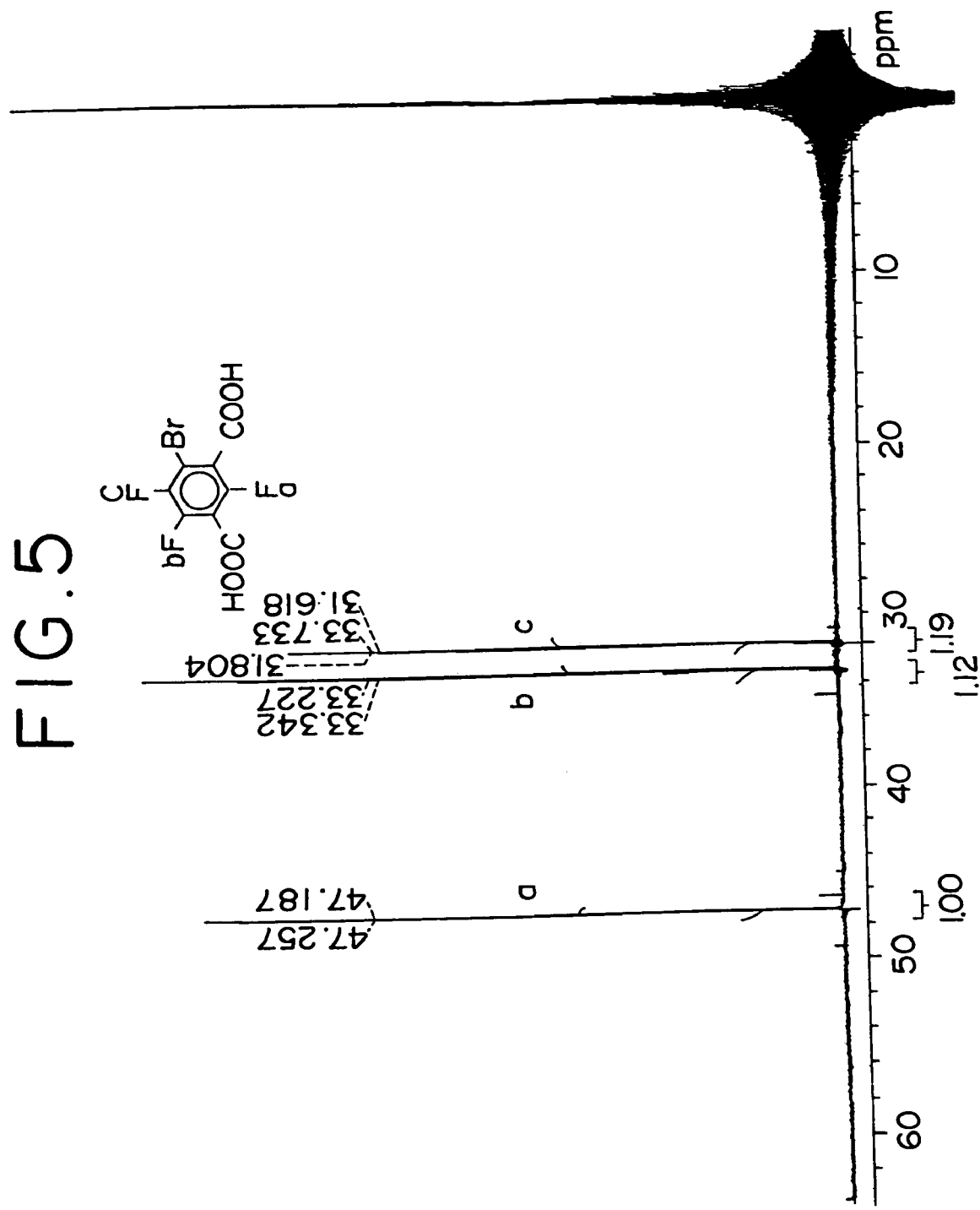
FIG. 5 shows a graph of $^{19}$F-NMR spectrum for 4-bromo-2,5,6-trifluoroisophthalic acid obtained in Synthesis Example III-4.

This product was measured by a mass spectrum analysis to be found M$^+$=298. When the product was analyzed by a $^{19}$F-NMR spectrometer, the spectrum depicted in FIG. 5 was obtained.

Example III-1

In a 5 liter reaction vessel, were placed 280.3 g (1.10 mol) of 5-chloro-2,4,6-trifluoroisophthalic acid obtained in Synthesis Example III-3, 815.1 g of tert-butanol and 266.7 g (2.64 mol) of triethylamine, and this mixture was heated to 80° C. with stirring. To the mixture, were dropped 726.9 g (2.64 mol) of diphenylphosphoryl azide over 2 hours with stirring. After dropping, the mixture was heated at 100° C. for additional 1 hour, and then cooled to 25° C. The solvent of tert-butanol was removed on an evaporator to give a brownish viscous liquid.

Then, in a separate 5 liter reaction vessel, were added the viscous liquid thus obtained and 915 ml of ethyl acetate, while stirring at room temperature 1200 ml of concentrated hydrochloric acid were dropped and additional stirring was continued for 18 hours. This reaction solution was diluted with 1500 ml of water, and then washed with chloroform. The washed reaction solution was neutralized with 5N aqueous NaOH solution, and then cooled to 25° C. to form a precipitate. After suction filtration, the residue was dissolved into 500 ml of toluene, washed with a saturated aqueous NaCl solution, and then dried with magnesium sulfate. After removal of the solvent (ethyl acetate) on an evaporator, the solid obtained was dried in vacuo at room temperature for 3 hours. After distillation of the solid obtained, by re-crystallization with a toluene-hexane mixed solution (volume ratio: 2:3), 117.6 g (0.60 mol) of a white solid of 5-chloro-2,4,6-trifluoro-m-phenylenediamine was produced (yield: 54.2%).

Figure 6:
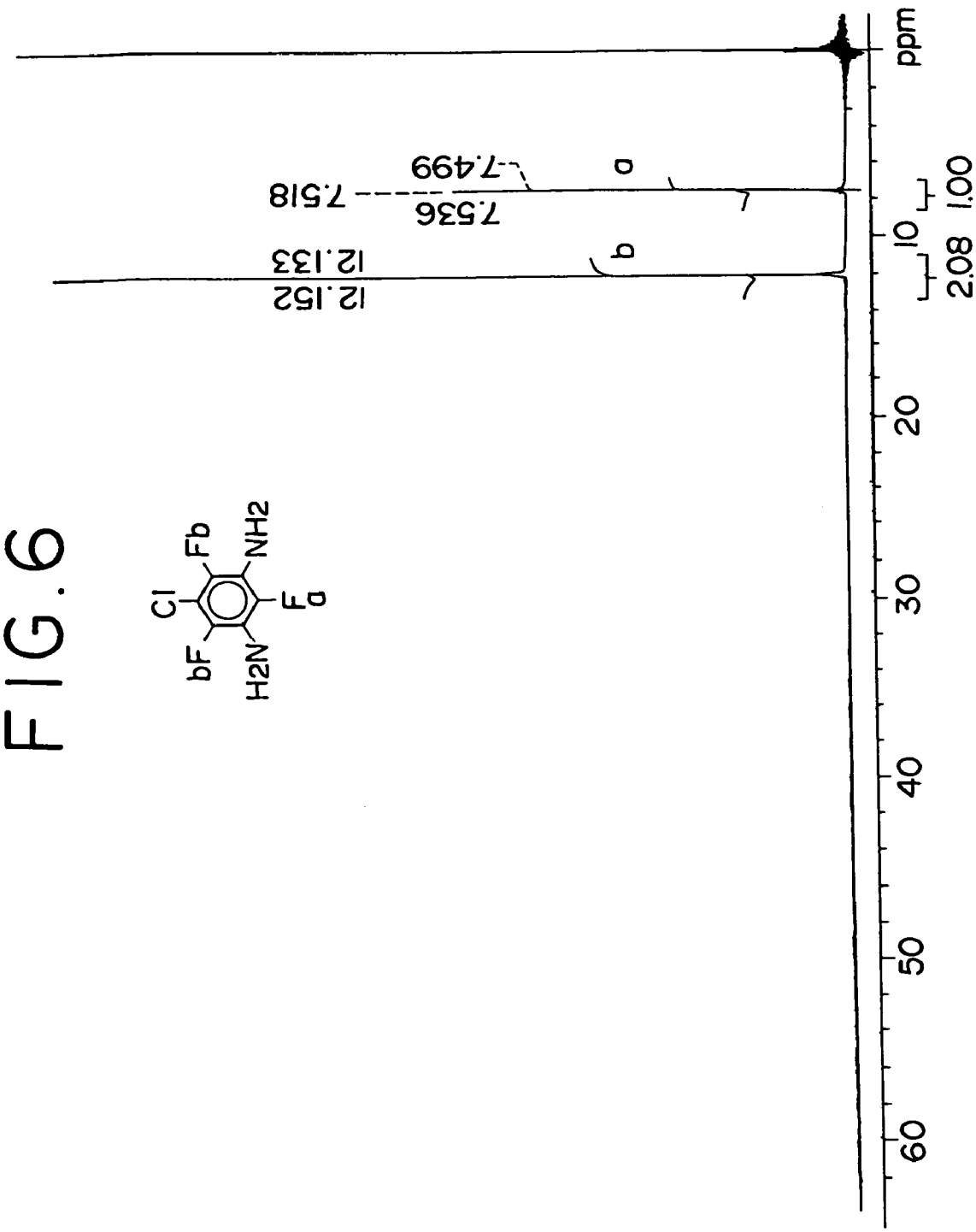
FIG. 6 shows a graph of $^{19}$F-NMR spectrum for 5-chloro-2,4,6-trifluoro-m-phenylenediamine obtained in Example III-1.

This product was measured by a mass spectrum analysis to be found M$^+$=196. When the product was analyzed by a $^{19}$F-NMR spectrometer, the spectrum depicted in FIG. 6 was obtained. Melting Point (FP800 Thermosystem available from Mettler in Germany): 132° C. The solubility to dimethylacetoamide at 25° C. was 68 wt. %. This solution was left standing for a night, but precipitations were not found.

Example III-2

In a one liter reaction vessel, were placed 16.9 g (56.52 mmol) of 4-bromo-2,5,6-trifluoroisophthalic acid obtained in Synthesis Example III-4, 260.8 g of tert-butanol, 11.6 g (114.64 mmol) of triethylamine and 31.4 g (114.04 mmol) of diphenylphosphoryl azide, and then this mixture was heated at 100° C. for 17 hours. This reaction solution was concentrated on an evaporator to remove the solvent, and then dissolved in 350 ml of chloroform. Then, this solution was washed with 150 ml of a saturated NaHCO$_3$ solution, 150 ml of 1% HCl and 150 ml of water twice, respectively, and then dried with magnesium sulfate. By removing the solvent on the evaporator, a brownish viscous liquid was obtained.

Then, in a 300 ml reaction vessel, were added the viscous liquid thus obtained, 140 ml of ethyl acetate and 23 ml of concentrated hydrochloric acid, and the mixture was stirred at 40° C. for 3 hours. After stirring, this reaction solution and 250 ml of water were added in a 500 ml of beaker, stirred for 30 minutes. After standing, 2-layers occurred. The separated oil layer (approximately 130 ml) and 200 ml of 5N aqueous NaOH solution were added in a 500 ml beaker, and then stirred for 15 minutes to form a white precipitate. This white precipitate was suction filtrated, and then washed with water to give 9.35 g of a slight brownish solid. This solid was re-crystallized in a toluene-hexane (1:1 by volume) mixed solution to give 7.14 g (29.62 mmol) of a white solid of 4-bromo-2,5,6-trifluoro-m-phenylenediamine (yield: 52.1%).

Figure 7:
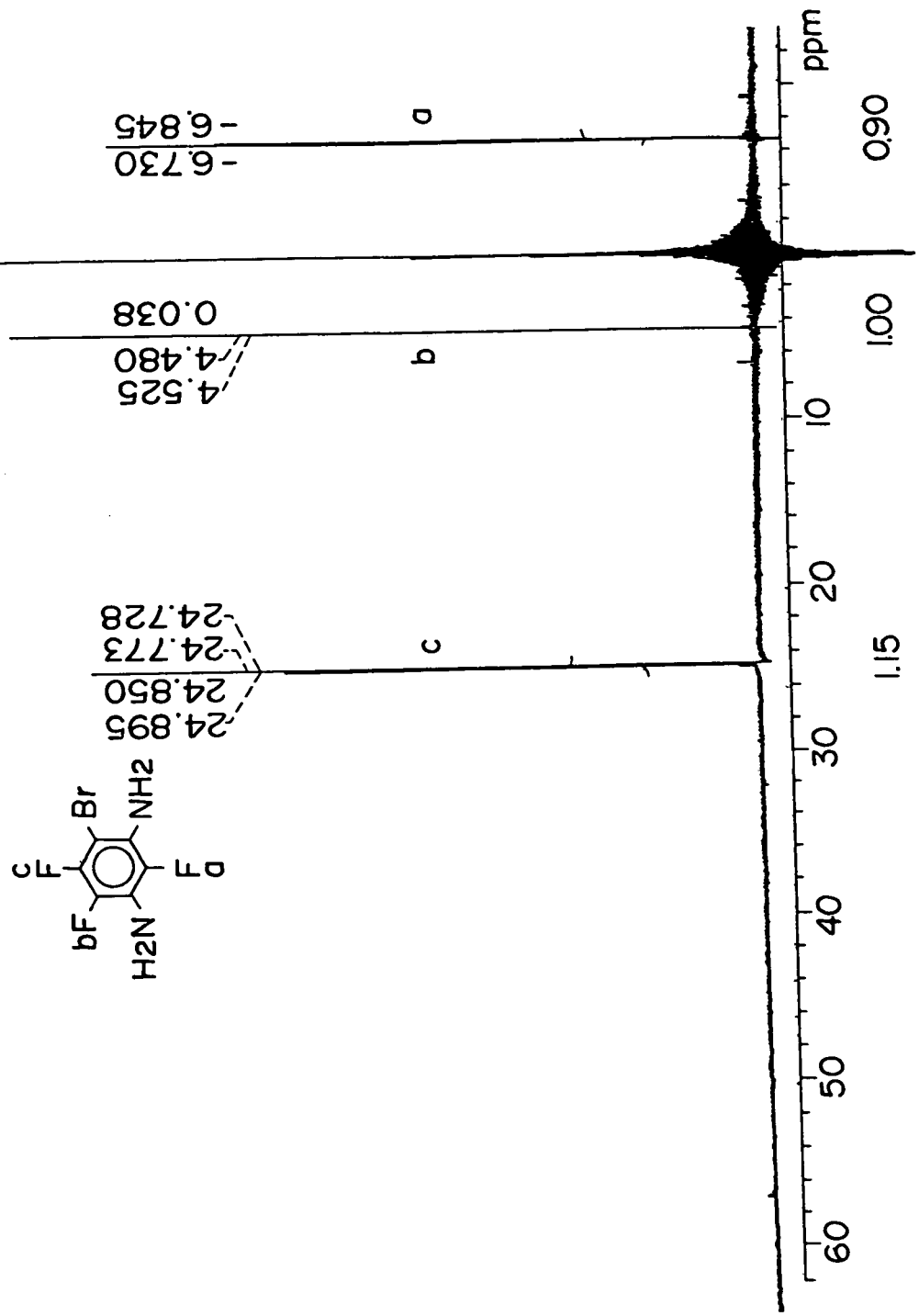
FIG. 7 shows a graph of $^{19}$F-NMR spectrum for 4-bromo-2,5,6-trifluoro-m-phenylenediamine obtained in Example III-2.

This product was measured by a mass spectrum analysis to be found M$^+$=240. When the product was analyzed by a $^{19}$F-NMR spectrometer, the spectrum depicted in FIG. 7 was obtained.

(Fluorine Compound)

Example IV-1

In a 3 liter reaction vessel, were added 200 g (1.00 mol) of tetrafluoroisophthalonitrile, 1 liter of N-dimethylformamide (DMF) and 102.7 g (1.00 mol) of NaBr. This mixture was heated at 120° C. for 1 hour. 3 Liter of water were added in a 5 liter beaker, and then the reaction solution thus obtained was added. After suction filtration, the residue was washed with water and hexane, and dried in vacuo to give 198.2 g of a white solid. After solid distillation, 142.8 g (0.55 mol) of a white solid of 4-bromo-2,5,6-trifluoroisophthalonitrile were obtained (yield: 55%).

Figure 8:
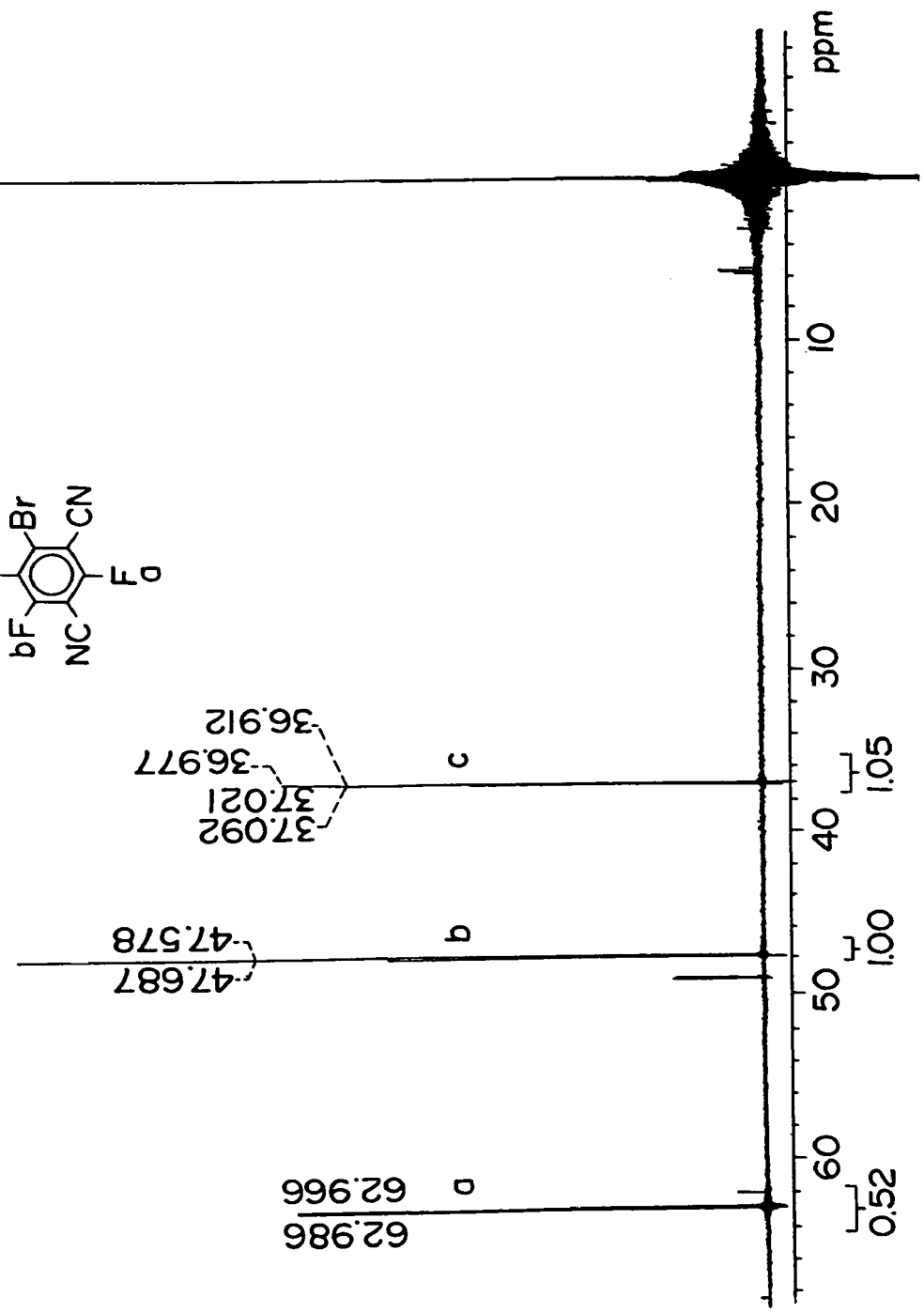
FIG. 8 shows a graph of $^{19}$F-NMR spectrum for 4-bromo-2,5,6-trifluoroisoptharonitrile obtained in Example IV-1.

This product was measured by a mass spectrum analysis to be found M$^+$=260. When the product was analyzed by a $^{19}$F-NMR spectrometer, the spectrum depicted in FIG. 8 was obtained.

Example IV-2

In a 200 ml 4-necked flask, were added 20.03 g (76.74 mmol) of 4-bromo-2,5,6-trifluoroisophthalonitrile, 40 ml of an aqueous 62% sulfuric acid solution and 40 ml of propionic acid, the mixture was refluxed at 130° C. for 18 hours. This solution was cooled to room temperature to precipitate a crystal. After suction filtration, the crystal was washed with a small amount of water. Then, the crystal was dissolved in 200 ml of IPE, and then washed with 100 ml of water and 100 ml of a saturated aqueous NaCl solution. Further, the crystal was dried with magnesium sulfate, and the IPE was removed on an evaporator to give 17.2 g (57.53 mmol) of a white solid of 4-bromo-2,5,6-trifluoroisophthalic acid (yield: 75.0%).

Figure 9:
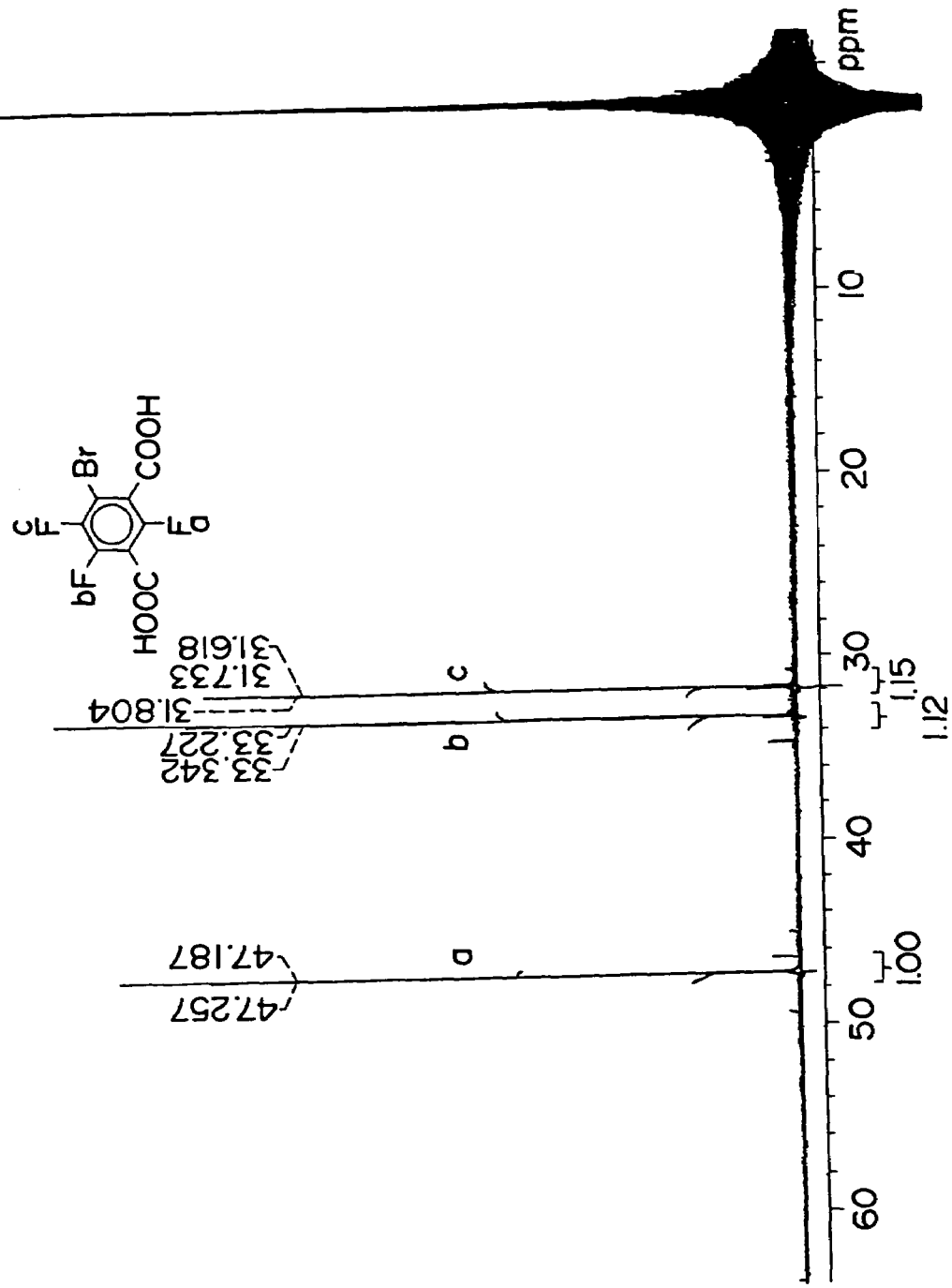
FIG. 9 shows a graph of $^{19}$F-NMR spectrum for 4-bromo-2,5,6-trifluoroisophthalic acid obtained in Example IV-2.

This product was measured by a mass spectrum analysis to be found M$^+$=298. When the product was analyzed by a $^{19}$F-NMR spectrometer, the spectrum depicted in FIG. 9 was obtained.

The entire disclosure of Japanese Patent Application Nos. 2001-142028, 2001-142029, 2001-142031 and 2001-142032 filed on May 11, 2001, respectively, including specifications, claims, drawings and summary are incorporated herein by reference in its entirety.

What is claimed is:

1. A halogen-containing aromatic acid dianhydride represented by the formula 1:

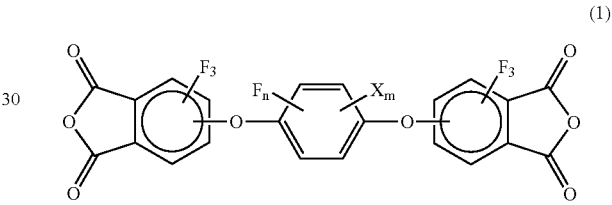

(1)

wherein X is a chlorine, bromine or iodine atom, m is an integer of 1 to 4, n is an integer of 3 to 0, and the sum of n and m is 4.

2. A dianhydride according to claim 1, wherein X is a chlorine atom, m is 4, and n is 0.

3. A dianhydride according to claim 1, wherein the dianhydride is 1,4-bis(3,4-dicarboxytrifluorophenoxy)tetrachlorobenzene dianhydride, 1,4-bis(3,4-dicarboxytrifluorophenoxy)tetrabromobenzene dianhydride, 1,4-bis(3,4-dicarboxytrifluorophenoxy)-2-chlorotrifluorobenzene dianhydride or 1,4-bis(3,4-dicarboxytrifluorophenoxy)-2-bromotrifluorobenzene dianhydride.

4. A dianhydride according to claim 1, wherein the dianhydride is 1,4-bis(3,4-dicarboxytrifluorophenoxy)tetrachlorobenzene dianhydride.

* * * * *